United States Patent
Kay et al.

(10) Patent No.: US 7,427,489 B1
(45) Date of Patent: Sep. 23, 2008

(54) SCREENING ASSAY TO IDENTIFY MODULATORS OF THE SLEEP/WAKE CYCLE

(75) Inventors: Steve A. Kay, San Diego, CA (US); John B. Hogenesch, Encinitas, CA (US); M. Fernanda Ceriani, Buenos Aires (AR); Satchidananda Panda, San Diego, CA (US)

(73) Assignees: The Scripps Research Institute, La Jolla, CA (US); IRM LLC, Hamilton (BM)

( * ) Notice: Subject to any disclaimer, the term of this patent is extended or adjusted under 35 U.S.C. 154(b) by 0 days.

(21) Appl. No.: 10/464,817

(22) Filed: Jun. 17, 2003

Related U.S. Application Data

(60) Provisional application No. 60/389,759, filed on Jun. 17, 2002.

(51) Int. Cl.
    *G01N 33/53* (2006.01)
(52) U.S. Cl. .......................... 435/7.21; 800/3
(58) Field of Classification Search .................. 435/7.1; 424/9.1
    See application file for complete search history.

(56) References Cited

U.S. PATENT DOCUMENTS

| | | | |
|---|---|---|---|
| 5,637,470 A | 6/1997 | Kaczorowski et al. | 435/7.21 |
| 6,107,066 A * | 8/2000 | Tsien et al. | 435/173.4 |
| 6,602,399 B1 * | 8/2003 | Fromherz et al. | 205/777.5 |

OTHER PUBLICATIONS

Toyota et al. 2002. Behavioral characterization of mice lacking histamine H3 receptors. Molecular Pharmacology 62:389-397.*
Barbier AJ et al. 2004. Acute wake-promoting actions of JNJ-5207852, a novel, diamine-based H3 antagonist. British Journal of Pharmacology 143:649-661.*
Hendricks, J.C. et al. 2000. Neuron 25:129-138.*
Dudley, C.A. et al., 2003. Science 301:379-383.*
O'Reardon et al. 2004. Obesity Research 12:1789-1796.*
Hille, B. Ionic channels of excitable membranes. 1992. Sunderland, MA:Sinauer Associates. pp. 4-19, 121-122.*
Prosser, R.A. et al. 1994. Brain Research 644:67-73.*
Mintz, E.M. 1999. Journal of Neuroscience 19:5124-5130.*
Lawson, K. 2000. Kidney International 57:838-845.*
Gillette, M.U. et al. 1999. Recent Progress in Hormone Research 54:33-59.*
Hille 1992. Ionic Channels of Excitable Membranes, Second Edition, pp. 24-27.*
Biello et al. 1997. Journal of Neuroscience 17:8468-8475.*
Challet 1998. Journal of Biological Rhytms 13:410-421.*
Kandel 1991. Principles of Neural Science, Third Edition, p. 107 and 180-181.*
Schwartz 1987. Proc Natl Acad Sci USA 84:1694-1698.*
Hanner et al. (1997) Proc Natl Acad Sci USA 94:2853-2858.*

Allada et al., "A mutant Drosophila homolog of mammalian Clock disrupts circadian rhythms and transcription of period and timeless", *Cell*, May 1998, 93(5):791-804.
Atkinson et al., "Molecular separation of two behavioral phenotypes by a mutation affecting the promoters of a Ca-activated K channel", *J Neurosci.*, Apr. 2000, 20(8):2988-93.
Butler et al., "mSlo, a complex mouse gene encoding "maxi" calcium-activated potassium channels", *Science*, Jul. 1993, 261(5118):221-4.
Ceriani et al., "Genome-wide expression analysis in Drosophila reveals genes controlling circadian behavior", *J Neurosci.* Nov. 2002, 22(21)9305-19.
Claridge-Chang et al., "Circadian regulation of gene expression systems in the Drosophila head", *Neuron*, Nov. 2001, 32(4):657-71.
Dunlap, "Molecular bases for circadian clocks", *Cell*, Jan. 1999, 96(2):271-90.
Gekakis et al., "Role of the CLOCK protein in the mammalian circadian mechanism", *Science*, Jun. 1998, 280(5369):1564-9.
Harmer, "For the times they are a-changing'—or are they?", *Anaesthesia*, Aug. 2000, 55(8):735-6.
Helfrich-Forster, "Robust circadian rhythmicity of Drosophila melanogaster requires the presence of lateral neurons: a brain-behavioral study of disconnected mutants", *J Comp Physiol.*, Apr. 1998, 182(4):435-53.
Ibata, "Functional morphology of the suprachiasmatic nucleus", *Front Neuroendocrinol.*, Jul. 1999, 20(3):241-68.
McDonald et al., "Microarray analysis and organization of circadian gene expression in Drosophila", *Cell*, Nov. 2001, 107(5):567-78.
McMahon et al., "The Bulla ocular circadian pacemaker. I. Pacemaker neuron membrane potential controls phase through a calcium-dependent mechanism", *J Comp Physiol.*, Aug. 1987, A161(3):335-46.
McWatters et al., "The ELF3 zeitnehmer regulates light signalling to the circadian clock", *Nature*, Dec. 2000, 408(6813):716-30.
Michel et al., "Circadian rhythm in membrane conductance expressed in isolated neurons", *Science*, Jan. 1993, 259(5092):239-41.
Pallank et al., "Cloning and characterization of human and mouse homologs of the Drosophila calcium-activated potassium channel gene, slowpoke", *Hum Mol Genet.*, Aug. 1994, 3(8):1239-43.
Panda et al., "Circadian rhythms from flies to human", *Nature*, May 2002, 417(6886):329-35.
Panda et al., "Coordinated transcription of key pathways in the mouse by the circadian clock", *Cell*, May 2002, 109(3):307-20.
Phillips et al., "CHRNB2 is the second acetylcholine receptor subunit associated with autosomal dominant nocturnal frontal lobe epilepsy", *Am J Hum Genet.*, Jan. 2001, 68(1):225-31.

(Continued)

*Primary Examiner*—Daniel E. Kolker
(74) *Attorney, Agent, or Firm*—DLA Piper US LLP

(57) ABSTRACT

Screening assays for identifying agents that modulate BK channel activity and further modulate the sleep/wake cycle in a subject, circadian regulated locomotor activity in a subject, or both are provided, as are agents identified using such screening assays. Also provided are methods of modulating the sleep/wake cycle in a subject and methods of modulating circadian regulated locomotor activity in a subject by administering an agent that modulates BK channel activity to the subject, for example, an agent identified by a screening assay as disclosed.

33 Claims, No Drawings

OTHER PUBLICATIONS

Schopperle et al., "Slob, a novel protein that interacts with the Slowpoke calcium-dependent potassium channel", *Neuron*, Mar. 1998, 20(3):565-73.

Stokkan et al., "Entrainment of the circadian clock in the liver by feeding", *Science*, Jan. 2001, 291(5503):490-3.

Toh et al., "An hPer2 phosphorylation site mutation in familial advanced sleep phase syndrome", *Science*, Feb. 2001, 291(5506):1040-3.

Wang et al., "Simultaneous binding of two protein kinases to calcium-dependent potassium channel", *J Neurosci.*, May 1999, 19(10):RC4 (1-7).

Wang et al., "Rhythmic expression of Nocturnin mRNA in multiple tissues of the mouse", *BMC Dev Biol.*, May 2001, 1(1):9.

Young et al., "Time zones: a comparative genetics of circadian clocks", *Nat Rev Genet.*, Sep. 2001, 2(9):702-15.

Zhou et al., "A dynamically regulated 14-3-3, Slob, and Slowpoke potassium channel complex in Drosophila presynaptic nerve terminals", *Neuron.*, Apr. 1999, 22(4):809-18.

\* cited by examiner

SCREENING ASSAY TO IDENTIFY MODULATORS OF THE SLEEP/WAKE CYCLE

This application claims the benefit of priority under 35 U.S.C. § 119(e) of U.S. Ser. No. 60/389,759, filed Jun. 17, 2003, the entire content of which is incorporated herein by reference.

This invention was made in part with government support under Grant No. NH51573 awarded by the National Institutes of Health. The government may have certain rights in this invention.

BACKGROUND OF THE INVENTION

1. Field of the Invention

The present invention relates generally to the circadian regulation of the sleep/wake cycle, and more specifically to methods of identifying agents that affect calcium activated potassium channel activity and thereby modulate the sleep/wake cycle, and to methods of modulating the sleep/wake cycle by affecting calcium activated potassium channel activity.

2. Background Information

Most organisms undergo a rhythmic pattern of sleep and wakefulness that cycles over a twenty-four hour period and generally is linked to the day/night cycle. In human adults, for example, sleep onset generally begins about four to five hours after nightfall, and spontaneous awakening occurs about one to two hours after sunrise (see Young and Kay, *Nat. Rev. Genet.* 2:702, 2001). Many individuals, however, suffer from abnormalities in the normal sleep/wake cycle, including, for examples, individuals that suffer from insomnia and individuals that suffer from disorders such as narcolepsy, in which sleep onset can occur at any time of day, or familial advanced sleep phase syndrome (FASPS), in which the time of sleep onset and awakening occur earlier than normal (see, for example, Young and Kay, supra, 2001).

A genetic mutation was recently linked to FASPS in humans, and is the first example of a genetic defect associated with a defect in the sleep/wake cycle in humans (Toh et al., *Science* 291:1040, 2001). The identification of such a mutated gene, and its normal counterpart, provide a means to develop assays for identifying drugs that correct, or at least decrease, the effect due to the mutation, thus allowing an individual with the mutation to have a more normal pattern of sleep and wakefulness. Although drugs that ameliorate the effect due to the mutation in FASPS will be a great help to individuals having that mutation, the drugs are not likely to be useful for individuals suffering from other sleep disorders such as insomnia. As such, the majority of individuals suffering from disorders of the sleep/wake cycle such as insomnia must continue to rely on relatively non-specific drugs, including prescription drugs such as benzodiazepine agonists and over-the-counter drugs, which often contain antihistamines. Such drugs, however, act generally and, while they can assist in helping a person sleep, they also can have undesirable side effects, including causing confusion and loss of balance.

Clearly, it would be preferable to identify additional specific genes involved in regulating the sleep/wake cycle so that individual suffering from sleep disorders so that the gene products could be used as targets in screening assays to identify drugs useful for specifically modulating the sleep/wake cycle. Microarray technology provides a means to identify the expression of a large number of genes in a single assay and, therefore, provides a powerful tool for identifying genes of interest, including those involved in regulating the sleep/wake cycle. A microarray is formed by linking a large number of discrete polynucleotide sequences, for example, a population of polynucleotides representative of a genome of an organism, to a solid support such as a microchip, glass slide, or the like, in a defined pattern. By contacting the microarray with a nucleic acid sample obtained from a cell of interest, and detecting those polynucleotides expressed in the cell that hybridize specifically to complementary sequences on the chip, the pattern formed by the hybridizing polynucleotides allows the identification of clusters of genes that are expressed in the cell. Furthermore, when each polynucleotide linked to the solid support is known, the identity of the hybridizing sequences from the nucleic acid sample can be identified.

Microarray technology provides a means to identify coordinate gene expression simply by comparing patterns of hybridization. For example, by comparing the hybridization pattern of nucleic acid molecules obtained from cells of an individual suffering from a disease with the nucleic acids obtained from the corresponding cells of a healthy individual, clusters of genes that are differentially expressed can be identified. The identification of such differentially expressed genes provides a means to identify new genes, and provides insight as to the pattern of gene expression that occurs in a normal organism or in an organism suffering from a pathologic condition.

Microarray technology further allows the identification of clusters of genes that are coordinately regulated and that encode proteins common to particular intracellular pathways. Thus, microarray technology has been used to determine that proteins involved in metabolic pathways such as photosynthesis in plants and cuticle formation and lipid metabolism in fruit flies are encoded by genes that are coordinately regulated and, further, that such coordinate expression is circadian regulated, i.e., cycles with approximately twenty-four hour periodicity corresponding to day and night.

Despite the large number of genes that have been identified as circadian regulated, the key gene or genes that determine the sleep/wake cycle in humans have remained elusive. The identification of such a gene or genes would provide a target for drugs that could be used, for example, to specifically induce sleep in individuals suffering from insomnia, without causing undesirable side effects common to currently used drugs. Thus, a need exists to identify genes that encode proteins that regulate the sleep/wake cycle. The present invention satisfies this need and provides additional advantages.

SUMMARY OF THE INVENTION

The present invention is based on the discovery that the cyclic expression of a calcium dependent potassium channel (BK channel) correlates to locomotor activity and anticipates the sleep/wake cycle. Accordingly, the present invention provides screening assays for identifying agents that modulate circadian regulated locomotor activity and agents that modulate the sleep/wake cycle in a subject; agents identified using such methods; and methods of utilizing such agents to modulate locomotor activity or the sleep/wake cycle in a subject.

The present invention relates to a method of identifying an agent that can modulate the sleep/wake cycle in a subject. Such a method can be performed, for example, by contacting a test system, which includes a BK channel, with an agent suspected of having the ability to modulate the sleep/wake cycle in the subject; detecting a change in activity of the BK channel in the presence of the agent as compared to the activity of the BK channel in the absence of the agent, thereby identifying an agent that modulates BK channel activity;

administering the agent that modulates BK channel activity to a test subject; and detecting a change in the sleep/wake cycle of the test subject due to administration of the agent that modulates BK channel activity, thereby identifying an agent that can modulate the sleep/wake cycle in a subject. The BK channel used in such a screening assay can be in an isolated form; can be contained in a membrane, which can be a synthetic membrane or an isolated naturally occurring membrane; or can be contained in a membrane of an intact cell, preferably ex vivo, including in a membrane of a cell that normally expresses the BK channel or in a membrane of a cell that has been genetically modified to express the BK channel.

The BK channel can be a BK channel of any species, preferably a eukaryotic species, including an invertebrate such as an insect or a nematode, or a vertebrate such as an amphibian, avian or mammalian species. In one embodiment, the BK channel is a *Drosophila* slowpoke (slo) polypeptide. In another embodiment, the BK channel is an ortholog of a *Drosophila* slo polypeptide, for example, a mammalian ortholog such as mouse slo (Kcnma1) polypeptide or a human slo polypeptide. In still another embodiment, the BK channel is a mutant BK channel, for example, a mutant *Drosophila* slo polypeptide.

A test system for practicing a method of the invention can contain a substantially purified BK channel polypeptide, and contacting with the agent can be performed in vitro, for example, in a test tube, in a well of a plate, or in a circumscribed position on a microchip. The BK channel also can be contained in and traverse a membrane. In one embodiment, the membrane is a synthetic membrane, for example, a liposome or synthetic lipid bilayer, having a first side and a second side, which can, but need not, be an interior side and an exterior side, wherein the BK channel traverses the membrane. In another embodiment, the membrane is a cell membrane, which is isolated from a cell. In one aspect of this embodiment, the cell membrane is obtained from a cell that naturally expresses the BK channel, which can be a wild type or a mutant BK channel, for example, a cell membrane isolated from a muscle cell or a nerve cell of a eukaryotic organism such as a mammal. In another aspect of this embodiment, the cell membrane is isolated from a cell that has been genetically modified to express a heterologous BK channel. The heterologous BK channel can be the only BK channel expressed in the cell membrane, or can be co-expressed with an endogenous BK channel, either or both of which can be a mutant BK channel.

In another embodiment, a method of the invention is practiced using a cell that is delimited by a cell membrane, wherein the BK channel is expressed in the cell membrane. The BK channel can be an endogenous BK channel, or can be a heterologous BK channel expressed, for example, from a polynucleotide introduced into the cell or into a cell from which the genetically modified cell is derived. A heterologous BK channel can be transiently expressed in the genetically modified cell, or the encoding polynucleotide can be stably maintained in the cell. In one embodiment, the cell expressing the BK channel is contacted with a test agent ex vivo, for example, in a cell culture or in a tissue or organ culture. Thus, the cell can be a mammalian cell such as a human nerve cell or muscle cell, which naturally expresses a BK channel, or can be a *Xenopus* oocyte, which is genetically modified to express a BK channel, for example, a *Drosophila* slo polypeptide or a homolog, ortholog, paralog, or variant thereof. In another embodiment, the cell is contacted in an organism in situ, wherein the organism can, but need not, be a transgenic organism containing cells expressing, for example, a heterologous BK channel.

In a screening assay of the invention, the test system, which can be a reaction mixture containing an isolated BK channel polypeptide or an isolated cell membrane, or an intact cell, can further contain a BK channel binding protein. The BK channel binding protein can be, for example, a *Drosophila* slo binding protein (slob) or a homolog, ortholog, paralog, or variant thereof. In some organisms such as mammals, the BK channel can be in the form of a heterodimer, including an α subunit, which is an ortholog of *Drosophila* slo and comprises the pore forming unit, and a β subunit, which has a regulatory activity. Accordingly, the BK channel binding protein in a test system can be β subunit of a BK channel, for example, a human β subunit.

BK channel activity, including a change in BK channel activity due to contact with a test agent, can be examined using any of various well known methods for measuring channel activity, including methods for detecting voltage gated activity and methods of detecting calcium ion gated activity. For example, BK channel activity can be detected using an electrophysiological method such as a patch-clamp assay or a voltage clamp recording. BK channel activity also can be detected using a method that directly or indirectly detects passage of molecules through the channel, for example, passage of a fluorescent dye such as fura-2 or indo-1 or of an ion such as rubidium ion, or a change in expression of a reporter gene due to a change in the calcium ion or potassium ion levels. BK channel activity also can be measured by detecting a conformational change in the BK channel structure that is indicative of channel activity, for example, a fluorescence resonance energy transfer assay, or using a physical method such as Fourier transform infrared resonance spectroscopy, Raman spectroscopy, fluorescence polarization, or atomic force microscopy. Where the steps for identifying an agent that modulates BK channel activity are adapted to a high throughput format, the means for detecting a change in BK channel activity is selected accordingly.

In a method of the invention, an agent suspected of having the ability to modulate the sleep/wake cycle is examined initially for the ability to modulate BK channel activity, then an identified agent that modulates BK channel activity is administered to a test subject to identify an agent that can modulate the sleep/wake cycle. An agent that modulates the sleep/wake cycle can be identified by detecting a change in the sleep/wake pattern of the subject, either in comparison to the sleep/wake pattern in the subject prior to administration of the test agent, or in comparison to a sleep/wake pattern characteristic of a normal population comprising the subject. Routine statistical analyses can be used to determine a sleep/wake cycle characteristic of a subject (prior to and/or after treatment with a test agent) or of a normal population.

An agent that modulates BK channel activity and is suspected of being able to modulate the sleep/wake cycle can be administered to the test subject in any convenient manner, including, for example, orally or by injection. The test subject can be any subject suitable for testing the agent for the ability to modulate the sleep/wake cycle. In general, a suitable test subject expresses BK channels in muscle cells, nerve cells, or both, wherein the BK channels are substantially similar to those used for identifying an agent that modulates BK channel activity. The test subject can naturally express the BK channel, which can be a wild type or mutant BK channel, or can be genetically modified to express the BK channels, for example, a transgenic non-human subject containing cells expressing the heterologous BK channel.

An agent that is suspected of having the ability to modulate the sleep/wake cycle and that is to be examined according to a method of the invention can have any chemical structure. As such, the agent can be a polynucleotide, a peptide, a peptidomimetic, a peptoid, or a small organic molecule. Since aspects of a method of the invention are adaptable to high throughput formats, the agents to be screened can include a library of agents, which can be a random library, variegated library, or the like. An agent that modulates the sleep/wake cycle can act by increasing BK channel activity or by decreasing BK channel activity, including by increasing or decreasing the activity of a mutant BK channel. Accordingly, the present invention also provides an agent that modulates the sleep/wake cycle in a subject, wherein the agent is identified according to a method as disclosed herein.

The present invention also relates to a method of identifying an agent that can modulate circadian regulated locomotor activity in a subject. Such a method can be performed, for example, by contacting a test system containing a BK channel with an agent suspected of having the ability to modulate circadian regulated locomotor activity in the subject; detecting a change in activity of the BK channel in the presence of the agent as compared to the activity of the BK channel in the absence of the agent, thereby identifying an agent that modulates BK channel activity; administering the agent that modulates BK channel activity to a test subject; and thereafter detecting a change in circadian regulated locomotor activity of the test subject, thereby identifying an agent that can modulate circadian regulated locomotor activity in a subject.

The present invention further relates to a method of modulating the sleep/wake cycle in a subject by administering an agent that modulates BK channel activity to the subject. The subject can be any subject in which it is desired to modulate the sleep/wake cycle. For example, the subject to be treated can be suffering from an acute or chronic sleep disorder, wherein administration of the agent modulates the sleep/wake cycle of the subject so as to more closely approximate the sleep/wake cycle of a normal population to which the subject belongs. The subject to be treated also can be one wishing to change his or her otherwise normal sleep/wake cycle, for example, in preparation for travel so as to avoid jet lag, or to facilitate adjustment to non-standard work hours such as a night shift.

The agent can be administered to a subject by any convenient means, including, for example, orally in the form of a tablet or a capsule, or as a component of food or water to which the subject has access. The agent also can be administered, for example, via a pump or can be formulated in a time-released form, thus providing a means to maintain the agent at a desired level over a period of time. A time-released form of the agent can be contained, for example, in a matrix, which can be administered to a subject intradermally, subcutaneously, or intramuscularly.

The present invention also provides a method of modulating circadian regulated locomotor activity in a subject by administering an agent that modulates BK channel activity to the subject. The subject can be any subject for which it desired to regulate locomotor activity in a circadian manner, including, for example, a human subject suffering from an anxiety disorder, or a herd of farm animals so as to more conveniently control the herd.

The present invention also relates to the identification of specific cellular proteins, in addition to the BK channel, that cycle in a circadian regulated manner in the suprachiasmatic nucleus and in the liver (see Table 5). The rhythmic cycling of these proteins in both the head and body indicates that the proteins are representative of basic components of a circadian clock. As such, these rhythmically cycling proteins, which include, for example, receptors, including hormone receptors, and enzymes, including kinases and phosphatases, provide additional targets useful in screening assays to identify agents that can modulate the sleep/wake cycle. In addition, the regulatory elements of the genes encoding these clock regulated proteins provide targets useful in screening assays for identifying agents that regulate the expression of the clock regulated proteins. In particular, the clock regulated proteins of Table 5 (below), and the regulatory elements of the genes encoding these proteins, can be used in high throughput screening assays, for example, wherein two or more of the proteins (or regulatory elements) are examined in parallel to identify agents that regulate the activity (or expression) of one or a plurality of the proteins.

DETAILED DESCRIPTION OF THE INVENTION

Most organisms have endogenous biological clocks that coordinate physiology and behavior to adapt to diurnal changes in the environment. In mammals, the suprachiasmatic nucleus (SCN) is the anatomical site of a master pacemaker that regulates rhythmic processes throughout the body. Recent work indicates that peripheral circadian clocks also exist, suggesting they may exert proximal regulation of physiology specific to their target tissues. In *Drosophila*, a number of key processes such as emergence from the pupal case, locomotor activity, feeding, and aspects of mating behavior are under circadian regulation. Although the mechanisms by which the molecular oscillations take place are generally understood, a clear link between gene regulation and downstream biological processes has not previously been established.

An oligonucleotide-based high density array that interrogates gene expression changes on a whole genome level was used to identify clock controlled output genes in *Drosophila* and in mice. As disclosed herein, a variety of physiological processes ranging from protein stability and degradation, signal transduction, heme metabolism and detoxification were found to be under circadian transcriptional regulation in *Drosophila* (Example 1; see, also, Panda et al., Nature 417: 329-335, 2002a, which is incorporated herein by reference). A comparison of rhythmically expressed genes in the fly head and body revealed that the clock has adapted its output functions to the needs of each particular tissue, thus indicating that tissue-specific gene expression is superimposed on clock control of gene expression. A cycling calcium dependent potassium channel protein, slowpoke (slo) was identified as providing a key step in linking the transcriptional feedback loop to rhythmic locomotor behavior. As disclosed herein, expression of slo correlated with regulation of the sleep/wake cycle in *Drosophila*.

Examination of circadian output genes in the mouse SCN, which includes the central clock, and in mouse liver, which is an important regulator of physiology, revealed that approximately 10% of detectably expressed transcripts in both tissues were under circadian control, and that almost all of these output genes were specific to either the SCN or liver (Example 2). In addition, twenty proteins were identified that cycled in both the head and body (Table 5). The cycling of these proteins in the head and body indicates they represent basic clock components. Genes encoding proteins in rate-limiting steps in pathways involved in endocrine regulation of physiology, energy metabolism, and the redox state of the cell, and genes coding for both intracellular and extracellular signaling components were clock regulated. Remarkably, clock-regulated expression of the Kcnma1 gene, which encodes a calcium activated potassium channel orthologous to that encoded by the *Drosophila* slo gene, also was identified in mouse SCN. These results indicate that cyclic potassium channel activity is involved in the coordination of the rhythmic locomotor activity associated with the sleep/wake cycle, in eukaryotic organisms.

Clusters of genes involved in specific various biological pathways were identified as being coordinately expressed in a circadian-regulated manner in *Drosophila* and in the mouse (see Examples 1 and 2). Furthermore, when circadian-regulated expression of gene clusters was examined in the fly head as compared to fly bodies, only a few transcripts cycled in both tissues (Example 1; see, also, Ceriani et al., *J. Neurosci.* 22:9305-9319, 2002, which is incorporated herein by reference). Similar results were obtained when cycling transcripts in the mouse SCN were compared to those cycling in mouse liver (Example 2; see, also, Table 5; see, also, Panda et al., *Cell* 109:307-320, 2002b, which is incorporated herein by reference). However, while common cycling transcripts in central (head) as compared to peripheral tissues were rare, many transcripts that cycled, for example, in fly heads also were expressed in the fly bodies, indicating that differential transcriptional regulation occurs with respect to these genes.

One of the fly genes identified to be circadian-regulated in fly heads, but not in fly bodies, was that encoding the slowpoke binding protein, slob, which binds to the calcium iondependent voltage gated potassium channel, slowpoke (see Example 1). McDonald and Rosbash (supra, 2001) reported circadian cycling of slob expression, and suggested that cycling slob, through its interaction with slo, could give rise to circadian oscillations in potassium channel activity. The authors further suggested that such circadian oscillations in potassium channel activity could affect resting membrane potential, which, in turn, would result in calcium ion oscillations that may underlie oscillations in neuropeptide staining reported in lateral neuron termini (Id.). Circadian cycling of slob expression also was reported by Claridge-Chang et al. (supra, 2001), who suggested that oscillating slob protein, through its interaction with slo, may be involved in rhythmic control of synaptic function, including synaptic plasticity, a process that may require sleep. Claridge-Chang et al. further demonstrated by in situ hybridization that slob mRNA expression occurred in the developing mushroom body of the fly larval brain, and corresponded with the region of larval brain receiving projections of lateral neurons (LNs), which comprise the circadian pacemaker cells, and, based on these observations, suggested that innervating LNs may be required for cycling slob expression (Id.).

Neither McDonald and Rosbash (supra, 2001) nor Claridge-Chang et al. (supra, 2001) reported whether expression of slo mRNA correlated with slo protein expression or whether slo protein levels cycle in fly brain. It is well recognized that mRNA expression does not necessarily correlate with translation of an encoded protein in cells, and even when mRNA is translated, there is not necessarily a correlation between the level of mRNA in the cells and the amount of protein generated. For example, the mammalian protein HIF-1α is constitutively expressed at the mRNA level, however, HIF-1α protein only is apparent following exposure to low oxygen conditions (*Proc. Natl. Acad. Sci., USA* 92:5510-5514, 1995). Furthermore, neither of the references correlate slo mRNA expression with rhythmic locomotor activity in anticipation of dusk and dawn or with regulation of the sleep/wake cycle.

As disclosed herein, slob mRNA cycled robustly in the heads of flies exposed to either entrained (LD) or free running (DD) conditions, peaking at about ZT18, but did not cycle in clk$^{jrk}$ flies, which are mutants that have impaired clock function (Example 1). Based on this result, expression of slo was examined and found to oscillate in phase with slob, with a peak expression at ZT20 (see Ceriani et al., supra, 2002; FIGS. 4A to 4C). Immunocytochemical analysis of whole fly brain mounts revealed that the slo protein was localized in a subset of the ventral LNs. In wild type flies, cycling of slo correlated with locomotor activity, which increased in anticipation of dawn and dusk. In comparison, flies containing slo mutations failed to show a change in activity in anticipation of dusk and dawn, even though total activity for wild type and slo mutant flies was approximately the same (see Ceriani et al., supra, 2002; FIG. 5). As such, the present disclosure extends previous observations by demonstrating that slo, regulates changes in locomotor activity in anticipation of dawn and dusk, thus indicating that slo is a key regulator of the sleep/wake cycle. Furthermore, clock regulated expression of the Kcnma1 gene, which is a slo ortholog in mice, paralleled that found in *Drosophila* (see Example 2), indicating that the factors regulating the sleep/wake cycle are evolutionarily conserved. Accordingly, the present invention provides methods of modulating the sleep/wake cycle and methods of modulating circadian regulated locomotor activity in an individual by increasing or decreasing calcium activated potassium channel ("BK channel") levels or activity; drug screening assays, which allow the identification of agents that increase or decrease BK channel activity and, therefore, can modulate circadian regulated locomotor activity or the sleep wake cycle; and agents identified using such a screening assay.

In addition to clock regulated BK channel gene expression, which is localized to the head, several genes that cycle in a circadian regulated manner in both the suprachiasmatic nucleus and liver of mice were identified (Table 5). The sequences of the polypeptides can be obtained by searching for the appropriate identifier in the NCBI database ("Refseq" in Table 5) or in the Unigene database ("Unigene" in Table 5), which also provides ready access to orthologs of the listed mouse polypeptides. The more generalized rhythmic cycling of the clock regulated proteins listed in Table 5 indicates that they represent basic components of the circadian clock. As such, these rhythmically cycling proteins, as well as the genes encoding them (particularly the regulatory elements of such genes), provide additional targets useful in screening assays to identify agents that can modulate the circadian clock in an organism.

Screening assays of the invention are exemplified herein with reference to the BK channel. It will be recognized, however, that screening assays of the invention also can be performed using one or more of the proteins shown in Table 5, except that the methods will utilize an assay useful for detecting a change in the activity or function of the particular protein or proteins used in the assay. For example, where the protein used in a screening assay of the invention is a kinase such as casein kinase 1, alpha 1 or adenylate kinase or a phosphatase such as protein tyrosine phosphatase, non-receptor type 16 or protein tyrosine phosphatase 4a1 (see Table 5), the screening assay will comprise contacting the kinase or phosphatase with a substrate for the kinase or phosphatase, and an agent to examined for the ability to modulate the kinase or phosphatase activity, wherein a change in such activity due to the agent identifies the agent as one that can modulate a circadian function in a subject expressing the protein in a clock regulated manner. In one embodiment, a screening assay of the invention comprises a high throughput assay, wherein at least two of the polypeptides of Table 5, including, if desired, the mouse BK channel and/or the mouse Per2 gene product, or at least two regulatory elements comprising the 5' untranslated regions of the gene sequences encoding such polypeptides, can be contacted in parallel with one or more agents to be examined for an ability to modulate the activity of one or more of the polypeptides (or regulatory elements), thus providing a means to identify an agent that modulates the activity or level of expression of one or more clock regulated proteins. If desired, such an agent then can be examined, for example, for an ability to modulate the sleep/wake cycle or other clock regulated biochemical or physiological activity of a subject.

Accordingly, in one embodiment, the a screening assay of the invention provides means of identifying agents that can modulate the sleep/wake cycle in a subject. As exemplified herein, a screening assay of the invention can be performed, for example, by contacting a test system, which includes a BK channel, with an agent suspected of having the ability to modulate the sleep/wake cycle in the subject; detecting a change in activity of the BK channel in the presence of the agent as compared to the activity of the BK channel in the absence of the agent, thereby identifying an agent that modulates BK channel activity; administering the agent that modulates BK channel activity to a test subject; and detecting a change in the sleep/wake cycle of the test subject due to administration of the agent that modulates BK channel activity due to administration of the agent.

In another embodiment, a screening assay of the invention provides a means of identifying agents that can modulate circadian regulated locomotor activity in a subject. Such a method can be performed, for example, by contacting a test system containing a BK channel with an agent suspected of having the ability to modulate circadian regulated locomotor activity in the subject; detecting a change in activity of the BK channel in the presence of the agent as compared to the activity of the BK channel in the absence of the agent, thereby identifying an agent that modulates BK channel activity; administering the agent that modulates BK channel activity to a test subject; and detecting a change in circadian regulated locomotor activity of the test subject due to administration of the agent.

As used herein, the term "BK channel" or "calcium activated potassium channel" refers to the high conductance channel that is present in neuronal tissue and smooth muscle of eukaryotic organisms and is gated by intracellular calcium ion concentration and membrane potential. For purposes of the present invention, a BK channel comprises at least a *Drosophila* slo polypeptide, or a homolog, ortholog, or paralog thereof (collectively "wild type" slo or BK channel), or a variant of a wild type slo polypeptide (e.g., mutant). Such channels, which, in organisms such as mammals, can contain an α subunit and a β subunit, also are referred to as "maxi-K channels", enable efflux of potassium ions when opened due to an increase in the intracellular calcium ion concentration or membrane depolarization (change in potential). A BK channel useful in a drug screening assay of the invention can be a BK channel of any species, preferably a eukaryotic species, including an invertebrate such as an insect or a nematode, or a vertebrate such as an amphibian, avian or mammalian species.

BK channels are well known in the art and exemplified by those encoded by the *Drosophila* slowpoke (slo) gene, as well as by eukaryotic orthologs of slo, including mammalian slo (also referred to as Kcnma1) gene products, for example, the mouse slo (mslo) and human slo (hslo) orthologs. The nucleotide and amino acid sequences of *Drosophila* slo (Atkinson et al., *Science* 253:551, 1991; Adelman et al., *Neuron* 9:209, 1992; GenBank Acc. No. NM_079762, each of which is incorporated herein by reference) are well known, as are those of orthologs such as the mouse Kcnma1 ortholog (Butler et al., *Science* 261:221, 1993; Pallanck and Ganetzsky, *Hum. Mol. Genet.* 3:1239, 1994; GenBank Acc. No. NM_010610, each of which is incorporated herein by reference), human Kcnma1 (see Butler et al., supra, 1993; Pallanck and Ganetzsky, supra, 1994; see, also, Dworetzky et al., *Brain Res. Mol. Brain. Res.* 27:189, 1994; Tsang-Crank et al., *Neuron* 13:1315, 1994; GenBank Acc. No. NM_002247, each of which is incorporated herein by reference), rat Kcnma1 (see, for example, GenBank Acc. No. NM_031828, which is incorporated herein by reference); rabbit Kcnma1 (see, for example, GenBank Ace. No. AF321818, which is incorporated herein by reference). In view of the conserved sequence homology of the exemplified *Drosophila* and mammalian BK channel nucleotide and amino acid sequences, it will be recognized that other wild type slo polynucleotides and variants thereof readily can be identified and used in the methods of the invention.

The BK channel (or other clock regulated gene product) used in a screening assay of the invention can be in an isolated form, for example, a BK channel expressed from a recombinant nucleic acid or generated using an in vitro translation or coupled transcription/translation reaction. An isolated BK channel also can be obtained from cells that normally express the channel using routine methods for isolating a polypeptide from a membrane fraction of cells or can be generated using chemical synthesis methods. As used herein, the term "substantially purified" or "isolated", when used in reference to a polypeptide or a polynucleotide, means that the polypeptide or polynucleotide is in a form other than that in which it exists in nature. In general, an isolated polypeptide or polynucleotide is relatively free of materials with which it is naturally associated with in a cell. For example, a substantially purified clock regulated gene product such as a BK channel can comprise at least about 10% of a mixture, generally at least about 25% of a mixture, usually at least about 50% of a mixture, and particularly about 90% or more of a mixture containing the polypeptide. A determination that a polypeptide or a polynucleotide is substantially purified can be made using well known methods, for example, by performing electrophoresis and identifying the particular molecule as a relatively discrete band. A substantially purified polynucleotide, for example, can be obtained by cloning the polynucleotide, or by chemical or enzymatic synthesis. A substantially purified polypeptide can be obtained, for example, by a method of chemical synthesis, or using methods of protein purification, followed by proteolysis and, if desired, further purification by chromatographic or electrophoretic methods.

It should be recognized, however, that an isolated BK channel polypeptide, for example, can be added to a reaction mixture or that an isolated polynucleotide encoding a BK channel polypeptide can be introduced into a cell. Nevertheless, the polypeptide or polynucleotide is considered to be (or have been) substantially purified because it is not in the form in which it exists in nature. Methods for isolating a polypeptide are well known and include, for example, extraction, precipitation, ion exchange chromatography, affinity chromatography, and gel filtration methods, including combinations of such methods. For example, a BK channel can isolated by affinity chromatography using an antibody or other protein that specifically binds the BK channel. BK channel binding proteins are disclosed herein and well known in the art.

A test system for practicing a method of the invention can contain a substantially purified BK channel polypeptide, and contacting with the agent can be performed in vitro, for example, in a test tube, in a well of a plate, or in a defined position on a microchip, thus allowing for high throughput screening of agents suspected of having the ability to modulate BK channel activity. Such an in vitro reaction generally is performed in an aqueous solution, which can contain buffers that maintain the reaction at a desired pH; salts such as those providing potassium ions and calcium ions; and other reagents useful for performing such a reaction.

A BK channel used in a method of the invention also can be contained in a membrane, including a synthetic membrane or an isolated naturally occurring membrane; or a membrane of an intact cell that normally expresses the BK channel or that has been genetically modified to express the BK channel. The membrane can be a synthetic membrane, for example, a liposome or a synthetic lipid bilayer. Generally, though not necessarily, a BK channel will traverse the cell membrane, in which case the cell membrane has a first side and a second side. Depending on the assay being performed, the first and second side can be opposite side of a surface formed by the membrane, or can be an interior side and an exterior side of a membrane that forms an enclosed volume.

A membrane containing a BK channel and useful in a method of the invention also can be a cell membrane that has been isolated from a cell. The cell membrane can be obtained from a cell that naturally expresses the BK channel, for example, a cell membrane isolated from a muscle cell or a nerve cell of a eukaryotic organism such as a mammal. The cell membrane also can be isolated from a cell that has been genetically modified to express a heterologous BK channel. In a cell membrane obtained from such a genetically modified cell, the heterologous BK channel can be the only BK channel expressed in the cell membrane, or can be co-expressed with an endogenous BK channel. Furthermore, in this and other aspects of a screening method of the invention, the BK channel can be a wild type BK channel or a mutant BK channel (see, for example, Elkins et al., *Proc. Natl. Acad. Sci., USA* 83:8415, 1986, which is incorporated herein by reference).

A drug screening assay of the invention also can be practiced using an intact cell, which is delimited by a cell membrane containing a BK channel. The cell can be a muscle cell, nerve cell, kidney cell, epithelial cell, or other cell that expresses an endogenous BK channel, or can be cell that is genetically modified to express a heterologous BK channel from a polynucleotide introduced into the cell or into a cell from which used in the assay is derived. As used herein, the term "genetically modified" refers to a cell containing a heterologous polynucleotide that has been introduced into the cell using a recombinant DNA method. The term "heterologous" is used herein to indicate that a polynucleotide or polypeptide is not endogenous to a cell (or isolated cell membrane) in which it is introduced or contained, or that the polynucleotide or polypeptide is part of a construct such that it is in a form other than it normally would be found in a cell. As such, a polynucleotide, for example, encoding a BK channel that is introduced into a cell is heterologous with respect to the cell, as is a polypeptide expressed therefrom. It should be recognized that such a heterologous polynucleotide or polypeptide can be identical to an endogenous polynucleotide or polypeptide that also can naturally be present in the cell; for example, an expressible mouse slo polynucleotide can be introduced into mouse muscle cells that express endogenous mouse slo polypeptide, such that the number of slo polypeptides expressed in the cell is increased, thus providing a means to increase the sensitivity of a screening assay of the invention.

A heterologous polynucleotide, which can encode a wild type or mutant BK channel polypeptide or BK channel binding protein, a reporter polypeptide, or other polypeptide as desired, can be transiently expressed in the genetically modified cell, or can be stably maintained in the cell. The polynucleotide can be contained in a vector, which can facilitate manipulation of the polynucleotide, including introduction of the polynucleotide into a target cell. The vector can be a cloning vector, which is useful for maintaining the polynucleotide, or can be an expression vector, which contains, in addition to the polynucleotide, regulatory elements useful for transcription and, where appropriate, translation of the polynucleotide. An expression vector can contain the expression elements necessary to achieve, for example, sustained transcription of the encoding polynucleotide, or the regulatory elements can be operatively linked to the polynucleotide prior to its being cloned into the vector. For example, the polynucleotide can be operatively linked to a tissue specific regulatory element, for example, a muscle cell specific regulatory element, such that expression of an encoded polypeptide is restricted to muscle cells. Muscle cell specific regulatory elements including, for example, the muscle creatine kinase promoter (Sternberg et al., *Mol. Cell. Biol.* 8:2896, 1988, which is incorporated herein by reference) and the myosin light chain enhancer/promoter (Donoghue et al., *Proc. Natl. Acad. Sci., USA* 88:5847, 1991, which is incorporated herein by reference) are well known in the art.

An expression vector (or the polynucleotide) generally contains or encodes a promoter sequence, which can provide constitutive, inducible, tissue specific, or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51, 1994; Flotte, *J. Bioenerg. Biomemb.* 25:37, 1993; Kirshenbaum et al., *J. Clin. Invest.* 92:381, 1993; each of which is incorporated herein by reference).

Viral expression vectors can be particularly useful for introducing a polynucleotide into a cell, including, where desired, a cell in a subject. Viral vectors provide the advantage that they can infect host cells with relatively high efficiency and can infect specific cell types. For example, a polynucleotide encoding a BK channel polypeptide such as *Drosophila* slo, mouse slo, human slo, or the like, can be cloned into a baculovirus vector, which then can be used to infect an insect host cell, thereby providing a means to produce large amounts of the encoded slo polypeptide. The viral vector also can be derived from a virus that infects cells of an organism of interest, for example, vertebrate host cells such as mammalian, avian or piscine host cells. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980, 1992; Anderson et al., *Nature* 392:25, Suppl., 1998; Verma and Somia, *Nature* 389:239, 1997; Wilson, *New Engl. J. Med.* 334:1185 (1996), each of which is incorporated herein by reference).

A polynucleotide encoding a clock regulated gene product such as a BK channel, or encoding a polypeptide that specifically interacts with the clock regulated gene product and is required for or facilitates its activity, for example, a BK channel binding protein, or encoding a reporter molecule, selectable marker, or the like, which can, but need not, be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. Accordingly, a polynucleotide can be introduced into a cell as a naked nucleic acid molecule, can be incorporated in a matrix such as a liposome or a particle such as a viral particle, or can be incorporated into a vector. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the polynucleotide contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events.

Generally, a polynucleotide encoding a clock regulated gene product, for example, a BK channel, is introduced into a cell with a polynucleotide encoding a selectable marker, which provides a means to select cells that contain the introduced polynucleotide. Selectable markers include, for example, those that confer antimetabolite resistance, for example, dihydrofolate reductase, which confers resistance to methotrexate (Reiss, *Plant Physiol.* (Life Sci. Adv.) 13:143-149, 1994); neomycin phosphotransferase, which confers resistance to the aminoglycosides neomycin, kanamycin and paromycin (Herrera-Estrella, *EMBO. J.* 2:987-995, 1983) and hygro, which confers resistance to hygromycin (Marsh, *Gene* 32:481-485, 1984), trpB, which allows cells to utilize indole in place of tryptophan; hisD, which allows cells to utilize histinol in place of histidine (Hartman, *Proc. Natl. Acad. Sci., USA* 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: Current Communications in Molecular Biology, Cold Spring Harbor Laboratory ed.); and deaminase from *Aspergillus terreus*, which confers resistance to Blasticidin S (Tamura, *Biosci. Biotechnol. Biochem.* 59:2336-2338, 1995). In addition, reporter molecules can act as markers that facilitate identification of a plant cell containing the polynucleotide encoding the marker include, for example, luciferase (Giacomin, *Plant Sci.* 116:59-72, 1996; Scikantha, *J. Bacteriol.* 178:121, 1996), green fluorescent protein (Gerdes, *FEBS Lett.* 389:44-47, 1996), and numerous others as disclosed herein or otherwise known in the art.

A cell expressing a BK channel can be contacted with a test agent ex vivo, for example, in a cell culture or in a tissue or organ culture. As disclosed herein, the cell can be a eukaryotic cell, for example, a mammalian cell such as a human nerve cell or muscle cell, which naturally expresses a BK channel, or a cell that is genetically modified to express a BK channel, for example, a *Xenopus* oocyte, which can be genetically modified to express a wild type or variant slo polypeptide (see, for example, U.S. Pat. No. 5,637,470). The cell to be contacted also can be present in situ in an organism, which can, but need not, be a transgenic organism containing cells expressing, for example, a heterologous BK channel.

In a screening assay of the invention, the test system, which can be a reaction mixture containing an isolated BK channel polypeptide or an isolated cell membrane, or an intact cell, can further contain a BK channel binding protein, for example, a *Drosophila* slo binding protein (slob), which is encoded by slob (GenBank Acc. No. AY060721; Schopperle et al., *Neuron* 20:565, 1998, each of which is incorporated herein by reference), or a homolog, ortholog or paralog of *Drosophila* slob, or a variant thereof. In some organisms such as mammals, the BK channel is formed as a heterodimer, including an α subunit, which is an ortholog of *Drosophila* slo and comprises the pore forming unit, and a β subunit, which has a regulatory activity and, for purposes of the present invention, is considered a BK channel binding protein. Thus, where a screening assay of the invention utilizes a mammalian slo protein, for example, a human slo protein, the assay can further include the BK channel β subunit, i.e., a human β subunit. Nucleotide and amino acid sequences encoding mammalian BK channel β subunits are well known (see, for example, U.S. Pat. No. 5,637,470; Meera et al., *FEBS Lett.* 382:84, 1996, each of which is incorporated herein by reference).

Although mammalian BK channels can comprise a heterodimer, it should be recognized that inclusion of the BK channel binding protein (i.e., β subunit) is not necessary for practicing a screening assay of the invention. For example, when mouse slo was expressed alone in *Xenopus* oocytes, large conductance, potassium ion selective channel activity characteristic of BK channels was observed, and the activity was sensitive to charybdotoxin (CbTX) and iberiotoxin (ITX), which are selective for BK channels (Butler et al., supra, 1993). In other experiments, oocytes genetically modified to express a human β subunit, alone, exhibited no measurable potassium currents different from those in control oocytes using whole oocyte and patch-clamp recording methods, whereas oocytes expressing only the human α subunit (hslo) exhibited large outward currents that were activated at positive membrane potentials, and blocked by CbTX and ITX (U.S. Pat. No. 5,637,470). Oocytes genetically modified to express the human α and human β subunits also exhibited outward potassium currents that were blocked by CbTX and ITX. The magnitudes of currents were similar to those observed in oocytes expressing only the α subunit. However, the outward currents in oocytes expressing the α and β subunits were activated at more negative potentials than oocytes expressing only the α subunit, and were activated by a BK channel activator that did not activate the channel in oocytes expressing only the α subunit (U.S. Pat. No. 5,637,470; see, also, Meera et al., supra, 1996). Thus, in a screening assay for identifying an agent that modulates the activity of a BK channel that comprises an α subunit and β subunit in nature, there can be advantages to practicing a method of the invention with a test system containing the BK channel (α subunit) and BK channel binding protein (β subunit). It will be recognized, however, that not all BK channel binding proteins bind all BK channels. For example, *Drosophila* slob binds *Drosophila* slo but does not bind mouse slo (Schopperle et al., supra, 1998), whereas human slo binds the human β subunit and the bovine β subunit, both of which up-regulate the slo (α subunit) channel activity (Meera et al., supra, 1996).

In view of the exemplified polynucleotides and encoded BK channel and BK channel binding protein polypeptides, it will be recognized that well known procedures and algorithms based on identity (or homology) to the exemplified sequences can be used to identify homologs, orthologs, and variants thereof useful in the screening methods of the invention (see, for example, U.S. Pat. No. 5,966,712, which is incorporated herein by reference). Such polynucleotides, for example, can be identified by performing a BLASTN search using the *Drosophila* slo or murine kcnma1 polynucleotides as query sequences and selecting those substantially similar sequences, for example, sequences having an E value $\leq 1 \times 10^{-8}$. Such homologous, orthologous or variant polynucleotides can be useful for performing the screening assays of the invention.

As used herein, the term "substantially similar", when used herein with respect to a nucleotide sequence, means a nucleotide sequence corresponding to a reference polynucleotide, wherein the corresponding sequence encodes a polypeptide having substantially the same structure and function as the polypeptide encoded by the reference polynucleotide. For purposes of the present invention, a reference (or query) sequence is a polynucleotide encoding a BK channel or a BK channel binding protein. Desirably the substantially similar nucleotide sequence encodes the polypeptide encoded by the reference nucleotide sequence. The percentage of identity between the substantially similar nucleotide sequence and the reference polynucleotide is at least 60%, generally at least 75%, particularly at least 90%, preferably at least 95%, and more preferably at least 99%. A nucleotide sequence "substantially similar" to a reference polynucleotide can selectively hybridize to the reference polynucleotide, but not to an unrelated polynucleotide, under hybridization conditions such as provided by incubation in 7% sodium dodecyl sulfate (SDS), 0.5 M NaPO$_4$, 1 mM EDTA at 50° C. with washing in 2×SSC, 0.1% SDS at 50° C.; generally by incubation in 7% SDS, 0.5 M NaPO$_4$, 1 mM EDTA at 50° C. with washing in 1×SSC, 0.1% SDS at 50° C.; particularly by incubation in 7% SDS, 0.5 M NaPO$_4$, 1 mM EDTA at 50° C. with washing in 0.5×SSC, 0.1% SDS at 50° C.; preferably by incubation in 7% SDS, 0.5 M NaPO$_4$, 1 mM EDTA at 50° C. with washing in 0.1×SSC, 0.1% SDS at 50° C.; and more preferably by incubation in 7% SDS, 0.5 M NaPO$_4$, 1 mM EDTA at 50° C. with washing in 0.1×SSC, 0.1% SDS at 65° C.

The term "substantially similar," when used in reference to a polypeptide sequence, means that an amino acid sequence relative to a reference (query) sequence shares at least about 65% amino acid sequence identity, generally at least about 75% amino acid sequence identity, particularly at least about 85%, preferably at least about 90%, and more preferably at least about 95% or greater amino acid sequence identity. Generally, sequences having an $E \leq 10^{-8}$ are considered to be substantially similar to a query sequence. Such sequence identity can take into account conservative amino acid changes that do not substantially affect the function of a polypeptide. As such, homologs or orthologs of the *Drosophila* and murine circadian-regulated genes, particularly *Drosophila* slo and murine kcnma1, variants thereof, and polypeptides (and encoding polynucleotides) substantially similar to those exemplified herein can be used for practicing the methods of the invention.

Homology or identity can be measured using sequence analysis software such as the Sequence Analysis Software Package of the Genetics Computer Group (University of Wisconsin Biotechnology Center, 1710 University Avenue, Madison, Wis. 53705). Such software matches similar sequences by assigning degrees of homology to various deletions, substitutions and other modifications. The terms "homology" and "identity," when used herein in the context of two or more polynucleotide or polypeptide sequences, refer to two or more sequences or subsequences that are the same or have a specified percentage of nucleotides or amino acid residues, respectively, that are the same when compared and aligned for maximum correspondence over a comparison window or designated region as measured using any number of sequence comparison algorithms or by manual alignment and visual inspection.

For sequence comparison, one sequence generally acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window" is used broadly herein to include reference to a segment of any one of the number of contiguous positions, for example, about 20 to 600 positions, for example, amino acid or nucleotide position, usually about 50 to about 200 positions, particularly about 100 to about 150 positions, in which a sequence may be compared to a reference sequence of the same number of contiguous positions after the two sequences are optimally aligned. Methods of alignment of sequence for comparison are well known in the art. Optimal alignment of sequences for comparison can be conducted, for example, by the local homology algorithm of Smith and Waterman (*Adv. Appl. Math.* 2:482, 1981), by the homology alignment algorithm of Needleman and Wunsch (*J. Mol. Biol.* 48:443, 1970), by the search for similarity method of Person and Lipman (*Proc. Natl. Acad. Sci., USA* 85:2444, 1988), each of which is incorporated herein by reference; by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF (see, also, U.S. Pat. No. 5,966,712). Such alignment programs can also be used to screen genome databases to identify polynucleotide sequences having substantially identical sequences to a polynucleotide encoding a BK channel polypeptide or BK channel binding protein.

A number of genome databases are available for comparison. Several databases containing genomic information annotated with some functional information are maintained by different organizations, and are accessible on the world wide web via the internet, for example, at the URLs "wwwtigr.org/tdb"; "genetics.wisc.edu"; "genome-www.stanford.edu/~ball"; "hiv-web.lanl.gov"; "ncbi.nlm.nih.gov"; "ebi.ac.uk"; "Pasteur.fr/other/biology"; and "genome.wi.mit.edu". In particular, sequences and expression characteristics of the circadian regulated expression of *Drosophila* and mouse genes as disclosed herein are accessible on the world wide web at the URL "expression.gnf.org/circadian".

The BLAST and BLAST 2.0 algorithms using default parameters are particularly useful for identifying polynucleotides encoding polypeptides substantially similar to the exemplified BK channel polypeptides and BK channel binding proteins (Altschul et al., *Nucleic Acids Res.* 25:3389-3402, 1977; *J. Mol. Biol.* 215:403-410, 1990, each of which is incorporated herein by reference). Software for performing BLAST analyses is publicly available on the world wide web through the National Center for Biotechnology Information at the URL "ncbi.nlm.nih.gov". This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra, 1977, 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4 and a comparison of both strands. For amino acid sequences, the BLASTP program uses as defaults a wordlength of 3, and expectations (E) of 10, and the BLOSUM62 scoring matrix (see Henikoff and Henikoff, *Proc. Natl. Acad. Sci., USA* 89:10915, 1989) alignments (B) of 50, expectation (E) of 10, M=5, N=−4, and a comparison of both strands.

The BLAST algorithm also performs a statistical analysis of the similarity between two sequences (see, for example, Karlin and Altschul, *Proc. Natl. Acad. Sci., USA* 90:5873, 1993, which is incorporated herein by reference). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

Protein and nucleic acid sequence homologies can be evaluated using the Basic Local Alignment Search Tool ("BLAST"). In particular, five specific BLAST programs can be used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (aligned) by means of a scoring matrix, many of which are known in the art. Preferably, the scoring matrix used is the BLOSUM62 matrix (Gonnet et al., *Science* 256:1443-1445, 1992; Henikoff and Henikoff, *Proteins* 17:49-61, 1993, each of which is incorporated herein by reference). Less preferably, the PAM or PAM250 matrices may also be used (Schwartz and Dayhoff, eds., "Matrices for Detecting Distance Relationships: Atlas of Protein Sequence and Structure" (Washington, National Biomedical Research Foundation 1978)). BLAST programs are accessible through the U.S. National Library of Medicine, for example, on the world wide web at the URL "ncbi.nlm.nih.gov".

An agent that is suspected of having the ability to modulate BK channel activity and, therefore, circadian regulated locomotor activity or the sleep/wake cycle (referred to generally herein as a "test agent"), can have any chemical structure. As such, the agent can be a polynucleotide, a peptide, a peptidomimetic, a peptoid, a small organic molecule, and the like. Furthermore, the screening methods of the invention are adaptable to high throughput formats and, therefore, conveniently allow the examination of libraries of test agents, including combinatorial libraries, which can be randomized, biased, or variegated (see, for example, U.S. Pat. No. 5,837,500, which is incorporated herein by reference). Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386, 1992; Markland et al., *Gene* 109:13-19, 1991; each of which is incorporated herein by reference); a peptide library (U.S. Pat. No. 5,264,563, which is incorporated herein by reference); a peptidomimetic library (Blondelle et al., *Trends Anal. Chem.* 14:83, 1995; a nucleic acid library (O'Connell et al., *Proc. Natl. Acad. Sci., USA* 93:5883, 1996; Tuerk and Gold, *Science* 249:505, 1990; Gold et al., *Ann. Rev. Biochem.* 64:763, 1995, each of which is incorporated herein by reference); an oligosaccharide library (York et al., *Carb. Res.*, 285:99, 1996; Liang et al., *Science,* 274:1520, 1996; Ding et al., *Adv. Expt. Med. Biol.*, 376:261-269, 1995; each of which is incorporated herein by reference); a lipoprotein library (de Kruif et al., *FEBS Lett.*, 399:232, 1996, which is incorporated herein by reference); a glycoprotein or glycolipid library (Karaoglu et al., *J. Cell Biol.*, 130:567, 1995, which is incorporated herein by reference); or a chemical library containing, for example, drugs or other pharmaceutical agents (Gordon et al., *J. Med. Chem.*, 37:1385, 1994; Ecker and Crooke, *BioTechnology,* 13:351, 1995; each of which is incorporated herein by reference).

An agent suspected of having the ability to modulate BK channel activity and, therefore, circadian regulated locomotor activity and/or a sleep/wake cycle in a subject can be a peptide. As used herein, the term "peptide" refers to a polymer comprising two or more amino acid residues or amino acid analogs that are covalently linked by a peptide bond, which can be a modified peptide bond. For example, a peptide test agent can contain one or more D-amino acids, or one or more amino acid analogs, for example, an amino acid that has been derivatized or otherwise modified at its reactive side chain. Similarly, one or more peptide bonds in the peptide can be modified, or the reactive group at the amino terminus or the carboxy terminus or both can be modified. Such peptides can be modified, for example, to have improved stability to a protease, an oxidizing agent or other reactive material the peptide can encounter in a biological environment, and, therefore, can be particularly useful for administration to a subject, which can be a test subject or a subject to be treated according to a method of the invention. Conversely, if desired, peptides can be designed to have decreased stability in a biological environment, for example, by including protease sensitive sites, such that the period of time the peptide is active in the environment is reduced.

A test agent also can be a polynucleotide. As used herein, the term "polynucleotide" means a polymer of two or more deoxyribonucleotides or ribonucleotides, or analogs thereof, that are linked together by a phosphodiester or other bond. As such, the terms include RNA and DNA, which can be a gene or a portion thereof, a cDNA, a synthetic polydeoxyribonucleic acid sequence, or the like, and can be single stranded or double stranded, as well as a DNA/RNA hybrid. Although the term "polynucleotide" is used herein to include naturally occurring nucleic acid molecules such as those encoding BK channel polypeptides, polynucleotides useful as test agents generally are non-naturally occurring molecules, which can be prepared, for example, by methods of chemical synthesis or by enzymatic methods such as by the polymerase chain reaction (PCR). Polynucleotides can be particularly useful as agents that modulate BK channel activity and, therefore, circadian regulated locomotor activity or sleep/wake cycle because nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference).

The nucleotides comprising a polynucleotide can be naturally occurring deoxyribonucleotides, such as adenine, cytosine, guanine or thymine linked to 2'-deoxyribose, or ribonucleotides such as adenine, cytosine, guanine or uracil linked to ribose; or nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220 (1994); Jellinek et al., *Biochemistry* 34:11363 (1995); Pagratis et al., *Nature Biotechnol.* 15:68 (1997), each of which is incorporated herein by reference). The covalent bond linking the nucleotides of a polynucleotide can be a phosphodiester bond, or any of numerous other covalent bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977 (1994); Ecker and Crooke, *BioTechnology* 13:351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified molecules can be less susceptible to degradation.

A polynucleotide containing naturally occurring nucleotides and phosphodiester bonds, can be chemically synthesized or can be produced using recombinant DNA methods, using an appropriate polynucleotide as a template. In comparison, a polynucleotide containing nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

An agent that modulates circadian regulated locomotor activity and/or the sleep/wake cycle can act by increasing BK channel activity or by decreasing BK channel activity, including by increasing or decreasing the activity of a mutant BK channel. Increased or decreased BK channel activity due to contact with a test agent can be examined using any of various methods known in the art for measuring potassium channel activity (see, for example, *Meth. Enzymol.: Ion Channels* (eds. Abelson et al., Academic Press 1998), which is incorporated herein by reference). For example, BK channel activity can be examined by making electrophysiological recordings such as by performing patch-clamp electrophysiologic analysis of cells following stable or transient transfection of cDNA molecules encoding slo and, if desired, slob or orthologs thereof, or voltage-clamp recording of *Xenopus* oocytes upon mRNA injection, cRNA, or cDNA injection. Extracellular or intracellular recordings of transfected cells can be obtained.

Extracellular voltage recording requires measurements of small biological potentials, often less than a millivolt in amplitude. The Axoclamp-2B, GeneClamp 500B and MultiClamp 700A microelectrode amplifiers are useful for such experiments (Axon Instruments, Inc.; Union City Calif.). Voltage clamp allows measurement of membrane current by monitoring the membrane voltage and injecting current to attain and maintain the desired voltage. As such, a voltage-clamp amplifier is selected based on its ability to measure voltage, and passes current in order to regulate the cellular voltage. Patch-clamp analysis utilizes a blunt pipette to isolate a patch of membrane. Patch-clamp recording can measure the individual ion channel currents that contribute to whole cell currents, and is compatible with current-clamp and voltage-clamp recording modes (see Axon Instruments, Inc., web site on the world wide web at URL "axon.com", information under "neurosciences" and "cellular neurosciences product lines"). In whole cell patch-clamping, the patch of membrane beneath the pipette is ruptured or otherwise made permeable such that currents passing through an entire cell membrane are recorded. This method is equivalent to intracellular recording with sharp microelectrodes, but has the advantage that it can be applied to cells that are very tiny or flat and would otherwise be very difficult to impale. The magnitude of the transmembrane current varies greatly between cell types. As such, the use of two electrodes, one for passing current and one for measuring voltage, is best for clamping large cells with large currents (Id.). Voltage clamp amplifiers such as the Axoclamp-2B amplifier and GeneClamp 500B amplifier are particularly useful for measurements using the Two-Electrode Voltage-Clamp (TEVC) mode (Axon Instruments, Inc.).

Current-clamp amplifiers are designed to control the current and measure the corresponding membrane voltage. It is common to pass current to stimulate a cell or modify its resting potential during intracellular voltage recording. The Axoclamp-2B amplifier, GeneClamp 500B amplifier, and MultiClamp 700A amplifier (Axon Instruments, Inc.) can pass current while in voltage-sensing (i.e., current-clamp) mode. The Axoclamp-2B amplifier also allows for "discontinuous" recording modes, applicable to both voltage clamp and current clamp. In this mode the instrument divides its time in passing current and recording voltage. The advantage of this mode is that the recording is free from the usual error due to the voltage drop across the electrode resistance, and can be used with a conventional intracellular microelectrode. Ion-selective electrodes, voltammetry and constant-voltage amperometry also can be used to measure levels and small changes in ion, neurotransmitter and hormone concentrations in tissues or in and near cells. These techniques require the ability to record small potentials and pass large currents. Ion-selective electrodes require differential input, low leakage current and high-impedance voltage following. The electrochemical techniques of voltammetry and constant-voltage amperometry are used to measure fast changes in neurotransmitter concentrations, and require a voltage-clamp amplifier with a command voltage range extended to ±1V (Axon Instruments, Inc.).

Detection of BK channel activity in native systems or in recombinant expression systems also can be examined using fluorescent dyes sensitive to membrane potential or intracellular ions (including pH). The Voltage Ion Probe Reader II system (VIPR II™ system) applies fluorescence resonance energy transfer (FRET) technology to ion channel analysis (Aurora Biosciences Corp., San Diego Calif.; see web site on the world wide web at the URL "aurorabio.com", information under "Aurora platforms" and "ion channel technology"). FRET is a distance-dependent interaction between the electronic excited states of two dye molecules, and is useful for investigating biological events that produce changes in molecular proximity, including, for example, FRET between a membrane-bound donor molecule and a mobile, voltage-sensitive, acceptor molecule to detect membrane potential ("Voltage Sensor Probe Technology"; Aurora Biosciences Corp.). The VIPR II™ system can be performed in a 96 well format or 384 well format and, therefore, is particularly suitable for high throughput screening assays, allowing for throughput of up to 40,000 samples per day under temperature controlled conditions. The system allows for dual emission fluorescence kinetic reading in real time, and includes data collection and analysis software. The system can screen potassium and calcium gated ion channels, reads approximately 5 mV changes in membrane potential in milliseconds, and allows for single cell detection.

Aurora Biosciences Corp. also provides "Voltage Sensor Probes" technology, which combine rapid response and high sensitivity for reliable detection of changes in membrane voltage induced by modulation of ion channels (see web site on the world wide web at the URL "aurorabio.com", information under "bioassay technologies" and "voltage sensitive probes"; see, also, "fluorescent probes"). Voltage Sensor Probes technology uses two fluorescent molecules, including oxonol, which is a highly fluorescent, negatively charged, hydrophobic ion that "senses" the transmembrane electrical potential, and coumarin lipid, which binds specifically to one face of the plasma membrane and functions as a FRET donor to the voltage-sensing oxonol acceptor molecule. In response to changes in membrane potential, oxonol can rapidly redistribute between two binding sites on opposite sides of the plasma membrane. When oxonol moves to the intracellular plasma membrane binding site upon depolarization, FRET is decreased and results in an increase in the donor fluorescence and a decrease in the oxonol emission (Id.).

Another fluorimetric system developed to measure channel activity is the fluorimetric imaging plate reader (FLIPR™) system (Molecular Devices Corp.; Sunnyvale Calif.; see web site on world wide web at URL "moleculardevices.com", search "FLIPR calcium assay"). The FLIPR™ system conveniently can be performed in a 384 well high throughput format (FLIPR$^{384}$) using a minimal sample volume. The FLIPR$_{384}$ system can monitor intracellular calcium, membrane potential, intracellular pH, and intracellular sodium from cells of a population in real time, providing maximum versatility and the ability to identify a potential hit seconds after it is added to the cell plate. Real-time, kinetic data also provides additional pharmacological information for ranking relative potencies of drugs, and gives information on the kinetics of the drug-receptor interaction (Id.).

BK channel activity also can be examined using an ion flux assay, for example, a rubidium ion efflux assay, which provides a functional analysis. Rubidium ion is similar in size and charge to potassium ion and confers similar permeability rates within the cell. BK channel activity can be determined by quantifying rubidium ion levels in cell lysate and supernatant fractions, wherein rubidium ion concentration in the fractions is directly related to channel efflux. Rubidium ion concentration can be determined using flame atomic absorption spectroscopy method, which can be automated using, for example, an ICR 8000 system (Aurora Biomed, Inc.; Vancouver BC; see, also, Aliphitiras et al., *Soc. Biomol. Screening,* 7th Ann. Conf., Poster Session 5, #5004, which is incorporated herein by reference).

Calcium ion flux also can be measured using dyes such as fura-2, indo-1, or derivatives thereof, which are UV light-excitable, ratiometric calcium ion indicators (Molecular Probes, Inc.; Eugene Oreg.). Fura-2, for example, is useful for ratiometric imaging, and exhibits an absorption shift that can be observed by scanning the excitation spectrum between 300 nm and 400 nm, while monitoring the emission at approximately 510 nm. In comparison, indo-1 is useful flow cytometry analysis. The emission maximum of indo-1 shifts from approximately 475 nm in calcium ion-free medium to about 400 nm when the dye is saturated with calcium ion. The sodium and potassium salts of fura-2 and the potassium salt of indo-1 are cell-impermeant probes that can be delivered into cells by microinjection or using an influx pinocytic cell-loading reagent (Molecular Probes, Inc.; see web site on world wide web at URL "molecularprobes.com", information under "Handbook" and "chapter 20"). Quin-2 is another calcium ion indicator that has lower absorptivity and quantum yield values than the fura-2 and indo-1 and, therefore, requires higher loading concentrations, which can buffer intracellular calcium ion transients (Id.).

BK channel activity also can be examined using ion chelators or other extracellular or intracellular reagents that exhibit a change in physico-chemical properties upon potassium binding, or by detecting changes in intracellular or extracellular pH levels (see, for example, U.S. Pat. No. 6,150,176; U.S. Pat. No. 6,140,132, each of which is incorporated herein by reference). In addition, changes in BK channel activity can be detected by examining changes in the expression of genes that are regulated by such changes, or by measuring the activity of calcium channels that are co-expressed with the BK channels and sensitive to membrane potential.

A change in BK channel activity also can be detected by examining the expression of a reporter gene that is operatively linked to a gene regulatory element that is responsive to the change in BK channel activity. For example, glucagon contains a calcium response element, which regulates glucagon expression in response to calcium ion concentration (Furstenau et al., *J. Biol. Chem.* 274:5851, 1999, which is incorporated herein by reference). As such, the calcium response element can be operatively linked to a reporter gene, which, upon introduction into a cell being examined according to a method of the invention, provides a means to detect changes in intracellular calcium ion due to an effect of a test agent on BK channel activity. Other gene regulatory elements that are responsive to changes in calcium ion include, for example, the cAMP response element and the serum response element (see, for example, Ginty, *Neuron* 18:183, 1997, which is incorporated herein by reference).

Reporter genes that can be operatively linked to a desired regulatory element are well known in the art and include, for example, a β-lactamase, chloramphenicol acetyltransferase, adenosine deaminase, aminoglycoside phosphotransferase, dihydrofolate reductase, hygromycin-B phosphotransferase, thymidine kinase, β-galactosidase, luciferase and xanthine guanine phosphoribosyltransferase polypeptide. Similarly, methods of detecting expression of such reporter genes are well known and include, for example, methods of detecting a colorimetric, luminescent, chemiluminescent, fluorescent, or enzymatic activity due to expression of the reporter polypeptide.

As used herein, the term "operatively linked" means that two or more molecules are positioned with respect to each other such that they act as a single unit and effect a function attributable to one or both molecules or a combination thereof. For example, a polynucleotide sequence encoding a reporter polypeptide or the like can be operatively linked to a regulatory element such as a calcium response element, in which case the regulatory element confers calcium inducible expression on the reporter similarly to the way in which the regulatory element would effect, for example, expression of glucagon in a pancreatic islet cell. A first polynucleotide coding sequence also can be operatively linked to a second (or more) coding sequence such that a chimeric polypeptide can be expressed from the operatively linked coding sequences. The chimeric polypeptide can be a fusion polypeptide, in which the two (or more) encoded peptides are translated into a single polypeptide, i.e., are covalently bound through a peptide bond; or can be translated as two discrete peptides that, upon translation, can operatively associate with each other to form a stable complex. For example, the fusion protein can comprise a fluorescent protein, which can be useful for constructing chimeric proteins for FRET analysis.

A change in BK channel activity also can be detected using a physical method such as Fourier transform infrared analysis, atomic force microscopy (Chen and Hansma, *J. Struct. Biol.* 131:44, 2000; Oesterhelt et al., *Science,* 143, 2000; Stolz et al., *J. Struct. Biol.* 131:171, 2000; Obregon et al., *Biophys. J.* 79:202, 2000, each of which is incorporated herein by reference), Raman spectroscopy, and the like, or by detecting a conformational change of the BK channel or a change in protein-protein interaction such as between the BK channel and a BK channel binding protein using a method such as FRET (U.S. Pat. No. 6,342,379; U.S. Pat. No. 5,661,035, each of which is incorporated herein by reference), B-RET, FIDA, FP, FCS. Such methods can be utilized for detecting changes in BK channel in a cell or changes in a substantially purified BK channel in vitro.

Various drugs can act as potassium channel antagonists and, therefore, can be useful for confirming the accuracy and validity of a test system comprising a BK channel and as controls that can be run in parallel with test agents. Such drugs include glyburide (1-{{{p-2-(5-chloro-o-anisamido) ethyl}phenyl}-sulfonyl}-3-cyclohexylurea), glipizide (1-cyclohexyl-3-{{{p-(2-(5-methylpyrazinecarboxamido) ethyl}phenyl}sulfonyl}urea) and tolbutamide (1-butyl-3-(p-methylbenzenesulfonyl)urea), which are used as antidiabetic agents, and other antagonists that are used as Class III anti-arrhythmic agents and to treat acute myocardial infarctions in humans. A number of naturally occurring toxins that block potassium channels, including apamin, IBX, CbTX, margatoxin, noxiustoxin, kaliotoxin, dendrotoxin(s), mast cell degranuating peptide, and β-bungarotoxin, also can be used for this purpose.

A screening assay of the invention provides a means to identify agent that can modulate circadian regulated locomotor activity and/or the sleep/wake cycle of an individual. As used herein, the term "sleep/wake cycle" refers to a rhythmic pattern, in which sleep onset leads to a period of sleep, followed by awakening from sleep, and a period of wakefulness, to be followed again by sleep onset, and so on. A normal sleep/wake cycle generally repeats in a circadian rhythm over a period of about 24 hours, and is linked to the length of day and night, i.e., the light/dark cycle. Reference herein to a "normal" or "typical" sleep/wake cycle means the sleep/wake cycle that is characteristic of a population of organisms in nature. For example, a normal sleep/wake cycle in humans includes sleep onset occurring about 4 to 5 hours after sunset, followed by a period of sleep that ends with awakening about 1 to 2 hours after sunrise (see, for example, Young and Kay, *Nat. Rev. Genet.* 2:702, 2001, which is incorporated herein by reference). In comparison, a normal sleep/wake cycle for nocturnal organisms is characterized by sleep onset occurring at or about sunrise or shortly thereafter.

Although actual sleep/wake cycles can vary substantially among individuals of a population, observation over a period of time and of specific individual or of a representative population of individuals and routine statistical analyses can be used to determine a sleep/wake cycle characteristic of the specific individual (prior to and/or after treatment with a test agent) or of the population, which can be a population of otherwise healthy individuals or a population of individuals suffering from the same disorder, for example, insomnia. It is recognized that in most populations, including humans, there will be a wide range of times "normal" individuals awaken or drowse to sleep. Nevertheless, any population of individuals will exhibit a normal distribution of such times and, therefore, an mean and standard deviation can be determined. For example, humans, on average, sleep for about eight hours and are awake for about sixteen hours.

Circadian rhythms are nearly ubiquitous in nature, occurring in prokaryotes and eukaryotes. The processes under circadian control are equally diverse, ranging from human sleep/ wake cycles to cell division in photosynthetic bacteria. The hallmark of these roughly 24 hour rhythms is their persistence under constant environmental conditions. This persistence is effected by the circadian clock, which is an internal biochemical oscillator. The circadian clock allows an organism to anticipate daily changes in the environment such as the onset of dawn and dusk, thereby providing the organism with an adaptive advantage (Yan et al., *Proc. Natl. Acad. Sci., USA* 95:8660, 1998). As such, the term "circadian regulated locomotor activity" is used herein to refer to rhythmic activity that is anticipatory of a daily change in the environment, particularly rhythmic activity that is anticipatory of the onset of dawn and dusk. In addition, the circadian clock regulates other rhythmic activities, including, for example, hormonal rhythms, blood pressure rhythms, body temperature rhythms, cholesterol production, and heme production. A normal pattern for a circadian regulated locomotor activity or other circadian regulated rhythmic activity can be determined by observing individuals in a population and analyzing the results using statistical methods, as discussed below with respect to determining a normal sleep/wake cycle. Such methods provide a standard value, from which individuals exhibiting an arrhythmia in the locomotor activity can be identified (see, also, Example 1).

In a screening assay of the invention, an agent suspected of having the ability to modulate circadian regulated locomotor activity and/or the sleep/wake cycle is examined initially for the ability to modulate BK channel activity, then agents that are identified as having the ability to modulate BK channel activity are administered to test subjects to identify those agents that also modulate circadian regulated locomotor activity, the sleep/wake cycle, or both. The test subject can be any organism that expresses wild type or mutant BK channels in nerve cells and muscle cells, including an organism that has been genetically modified to express such BK channels, for example, a transgenic non-human organism. Generally, the test subject contains cells that express substantially the same BK channels as were used in the initial test system to identify agents that modify BK channel activity. However, the test subject also can contain cells that express a homolog, ortholog or paralog of the BK channel used in the initial test system, or a mutant or other variant of the BK channel. In addition, the screening method can include one or more control subjects, which, for example, contain cells that express a BK channel that is not modulated by the test agent, thus providing a means to confirm the specificity of an agent that is found to modulate the sleep/wake cycle or circadian regulated locomotor activity of a test subject.

A test subject is selected, in part, based on the characteristics desired of the test agent being examined. For example, if test agents are being screened to identify those that can shift sleep and awakening by a desired time (e.g., about four, six, eight or twelve hours), the test subjects can be organisms that exhibit a normal sleep/wake cycle. In this respect, it should be recognized that many organisms, including experimental organisms such as mice, are primarily nocturnal. As such, while in humans, a "normal" sleep/wake cycle includes awakening about dawn (CT0) and drowsing to sleep after dusk (CT12), for example, at about CT16 (assuming an average of 8 hours sleep), the cycle can be different in an experimental organism that is used as a test subject for identifying an agent that would be useful in humans. Nevertheless, the effectiveness that an agent being tested in an experimental animal can have in a human can be determined by accounting for these differences. Where a test agent is being examined, for example, to treat insomnia, the test subject can be selected based on having symptoms of insomnia, or can be placed in conditions that are not conducive to sleep, and the ability of an agent that modulates BK channel activity to allow sleep to begin at a normal time can be examined. Where a test agent is being examined for an ability to induce circadian regulated locomotor activity, the test subject is selected based on a lack of such regulated activity, for example, a test subject exhibiting anxiety or hyperkinetic activity, or a subject exhibiting a circadian related sleep disorder such as familial advance phase sleep disorder or familial delayed phase sleep disorder (see, for example, *Sleep* 22:616-623, 1999).

An agent that modulates the sleep/wake cycle can be identified by detecting a change in the sleep/wake pattern of the subject, either in comparison to the sleep/wake pattern in the subject prior to administration of the test agent, or in comparison to a sleep/wake pattern characteristic of a normal population comprising the subject. The agent can be administered to the test subject (or control subject) in any convenient manner, including, for example, orally or by injection (see, also, below). Using such a screening assay as disclosed herein, agents that modulate the sleep/wake cycle or circadian regulated locomotor activity in a subject by modulating BK channel activity can be identified. Accordingly, the present invention provides agents identified by a screening assay. Such agents can be useful as medicaments for treating a subject having, for example, a disorder affecting the sleep/wake cycle.

The present invention also provides a method of modulating the sleep/wake cycle in a subject by administering an agent that modulates the activity of a clock regulated gene product, for example, BK channel activity, to the subject. The subject can be any subject in which it is desired to modulate the sleep/wake cycle. Generally, a subject to be treated is one suffering from an acute or chronic sleep disorder, wherein administration of the agent modulates the sleep/wake cycle of the subject so as to more closely approximate the sleep/wake cycle of a normal population to which the subject belongs. A sleep disorder amenable to treatment according to a method of the invention is characterized, in part, by an inability of the subject to establish a regular pattern of sleep, for example, insomnia or narcolepsy. A subject to be treated also can be one wishing to change his or her otherwise normal sleep/wake cycle. For example, a person preparing to travel to a different time zone, particularly a time zone that is at least about four hours or six hours different from that in which the person is leaving, can take an agent that delays (or advances) the current sleep/wake cycle a sufficient amount such that the person can avoid jet lag. Similarly, a person that works a night shift can benefit from a change in an otherwise normal sleep/wake cycle to one that accommodates his or her work schedule. As such, a method of the invention can provide advantages to the general public, including, for example, decreased risk of injuries due to tiredness during a night shift, or increased productivity of business person traveling to a distant time zone.

The present invention also provides a method of modulating circadian regulated locomotor activity in a subject by administering an agent that modulates BK channel activity to the subject. The subject can be, for example, a person suffering from an anxiety or hyperkinetic disorder, wherein administration of agent that attenuates the locomotor activity associated with the disorder provides a rhythmic decreased locomotor activity. Such a rhythmic decreased locomotor activity can be timed, for example, such that the subject can remain in a more "relaxed state" during work or school hours. A method of the invention also can be useful for treating a herd of farm animals, such that individual animals in the herd are not overly disruptive or such that the herd, in general, is more amenable to handling during desired times.

The agent can be administered to a subject by any convenient means, including, for example, orally in the form of a tablet or a capsule, or as a component of food or water to which the subject has access. The agent also can be administered, for example, via a pump or can be formulated in a time-released form, thus providing a means to maintain the agent at a desired level over a period of time. A time-released form of the agent can be contained, for example, in a matrix, which can be administered to a subject intradermally, subcutaneously, or intramuscularly.

Generally, for administration to a subject, the agent is formulated in a composition suitable for administration to the subject. As such, the present invention also provides compositions containing an agent, which modulates BK channel activity and further modulates the sleep/wake cycle or circadian regulated locomotor activity, in a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the agent and on the route of administration of the composition, which can be, for example, orally or parenterally such as intravenously, and by injection, intubation, or other such method known in the art.

The agent can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials, as are cationic liposomes, which can be modified with specific receptors or ligands, for example, to target muscle tissue or brain (Morishita et al., *J. Clin. Invest.*, 91:2580-2585 (1993), which is incorporated herein by reference).

The route of administration of a composition containing an agent that modulates the sleep/wake cycle or circadian regulated locomotor activity will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are well known (see, for example, Blondelle et al., supra, 1995; Ecker and Crook, supra, 1995). In addition, a polypeptide agent can be prepared using D-amino acids, or can contain one or more domains based on peptidomimetics, which are organic molecules that mimic the structure of peptide domain; or based on a peptoid such as a vinylogous peptoid.

A composition as disclosed herein can be administered to an individual by various routes, including, for example, topically, orally or parenterally, such as intravenously, intramuscularly, subdermally, or subcutaneously, or by passive or facilitated absorption through the skin using, for example, a skin patch or transdermal iontophoresis, respectively, or using a nasal spray or inhalant, in which case one component of the composition is an appropriate propellant. Preferably, the composition is administered orally, for example, as a component of a food or beverage, or is administered in a time released formulation. Where a group of subjects is to be treated, for example, a herd of farm animals, the composition can be incorporated in the livestock food or water.

One skilled in the art would know that the amount of the composition to administer to a subject depends on many factors including the age and general health of the subject as well as the route of administration. In view of these factors, the skilled artisan would adjust the particular dose as necessary. Appropriate amounts having the desired efficacy can be determined using routine methods. When humans are to be treated, the formulation of the composition and the routes and frequency of administration are determined, initially, using Phase I and Phase II clinical trials.

A composition for oral administration can be formulated, for example, as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those described above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695). Additional formulations can be determined based on the particular subjects to be treated.

The following examples are intended to illustrate but not limit the invention.

EXAMPLE 1

Circadian-Regulated Genes in *Drosophila*

This example provides a method for identifying the expression of circadian-regulated plant genes (see, also, Ceriani et al., supra, 2002).

Circadian behaviors take place at regular intervals due to the action of a cell autonomous clock, which marks time even in the absence of environmental information. This molecular clock relies on negative feedback loops, in which the positive driving forces control the expression of the negative components, which, in turn, block transcription at their own promoters (Young and Kay, supra, 2001). This oscillation at the mRNA level is only the first step towards sustainable molecular rhythms, which are accomplished by introducing a number of "delays" affecting message stability (Suri et al., *EMBO J.* 18:675, 1999), protein stability (Kloss et al, *Cell* 94:97, 1998) or controlling subcellular localization (Saez and Young, *Neuron* 17:911, 1996).

Although there is a relatively good understanding of how these molecular oscillations are generated, a clear link between the oscillator and the downstream biological processes under clock control has not been identified. Previous attempts to describe the extent of circadian transcriptional regulation identified a handful of clock-controlled "output" genes. A cDNA library screening identified about 20 oscillating mRNAs, most of which have unknown functions (Van Gelder et al., *Curr. Biol.* 5:1424, 1995). Alternative approaches included the screening of subtractive cDNA libraries, which retrieved circadian regulated gene-1 (Rouyer et al., *EMBO J.* 16:3944, 1997) and takeout (Sarov-Blat et al., *Cell* 101:647, 2000 and differential display, which identified vrille (vri, (Blau and Young, *Cell* 99:661, 1999).

To carry out a more global examination of clock-controlled transcription, high density oligonucleotide-based arrays were used. This approach was successfully employed in *Arabidopsis* uncovering an astonishing range of physiological processes under circadian control (Harmer et al, supra, 2000).

Clock-Controlled Transcription at all Times

Steady-state RNA levels were followed using DNA GeneChip™ microarrays (Affymetrix) spanning the entire *Drosophila* genome. Temporal profiling of 13,500 probe sets was carried out with a 4 hr time resolution during two consecutive days under "entrained" (light-dark cycles) and "free-running" (in constant darkness) conditions. Time courses for the DNA chipping experiments were carried out using *Drosophila* yw as wild type control, and yw/clk$^{jrk}$ as the mutant with impaired clock function. Newly enclosed wild type or mutant flies were entrained for 5 days to a 12 hr: 12 hr light:dark regime under constant temperature (25° C.). Time courses were performed either under light-dark (LD or "entrained") or under constant dark (DD or "free-running") conditions. Samples were collected every 4 hr for 2 consecutive days, and immediately frozen in dry ice. Heads and bodies were kept apart for RNA/protein extraction.

For the DD time courses flies were entrained to LD cycles during 5 days, then released into constant darkness; samples were taken during the first and second days in DD. Total RNA was prepared from fly heads or bodies homogenized in TRIZOL reagent (Invitrogen Corp., Carlsbad Calif.). RNA was purified using RNeasy kit (Qiagen). 7.5 μg of total RNA were hybridized to *Drosophila* GeneChip™ microarrays (Affymetrix). cDNA synthesis, biotin-labeling of cRNA, and hybridization of the chips were carried out as recommended by the manufacture. Data analyses were performed using Microarray Suite™ software (Affymetrix) and GeneSpring™ software (Silicon Genetics) software packages. Each sample was hybridized to two DNA GeneChip™ microarrays to test the reproducibility of the technique (Harmer et al., supra, 2000). The mean hybridization signal strength and the standard error of the mean for each probe set was calculated from the duplicate hybridizations.

To identify the cyclic mRNAs among the pool of expressed genes COSOPT, which is an analytical algorithm developed for detection and statistical characterization of rhythmic gene expression in gene array experiments was used. Briefly, data is fit to 100,000 cosine test waves and the significance of each fit is then determined empirically by temporally randomizing the data sets; those genes whose traces fit a cosine wave with a period between 20 and 28 hours are scored as cycling with a given probability.

COSOPT imports data and calculates the mean expression intensity and its corresponding standard deviation (SD). It then performs an arithmetic linear-regression detrend of the original time series. The mean and SD of the detrended time series are then calculated. COSOPT does not standardize the linear-regression detrended time series to standard normal deviates, thus allowing COSOPT to quantitatively assess oscillatory amplitude much more directly. Variable-weighting of individual time points (as in SEMs from replicate measurements) can be accommodated during analysis for the presence of rhythms in terms of a user-specified number and range of periods (test periods spaced uniformly in period-space).

Specifically, for each test period, 101 test cosine basis functions (of unit amplitude) are considered, varying over a range of phase values from (plus one-half the period) to (minus one-half the period), i.e., such that phase is considered in increments of 1% of each test period. COSOPT calculates, for each test cosine basis function, the least-squares optimized linear correspondence between the linear-regression-detrended data, ylr(x), and the test cosine basis function, yb(x), as a function of x, i.e., such that the approximation of ylr(x) by the test cosine basis function, yb(x), is optimized across all values, x, in terms of two parameters, ALPHA and BETA, whereby ylr(x)~ALPHA+BETA*yb(x). The quality of optimization possible by the test cosine basis function is quantitatively characterized by the sum of squared residuals between ylr(x) and the approximation given by {ALPHA+BETA*yb(x)} (referred to as CHI2, for Chi-squared).

The values of CHI2 are used to identify the phase at which the optimal correspondence between ylr(x) and yb(x) is obtained for each test period, i.e., the phase giving the smallest CHI2 value corresponds to the optimal phase. Thus, for each test period are assessed these values of ALPHA, BETA, and CHI2 at the optimal phase. Interpretively, BETA now represents an optimized, parametrized measure of the magnitude of the oscillatory amplitude expressed by ylr(x) in relation to, or as modeled by, a cosine wave of the corresponding period and optimal phase. Empirical resampling methods are employed to assess statistical probabilities of significance directly in terms of this parameter BETA at each test period and corresponding optimal phase, thus assessing statistically the probability that a significant rhythm is present in ylr(x) (in relation to or as modeled by a cosine functional form of the corresponding period and optimal phase).

One thousand Monte Carlo cycles are carried out, in which surrogate realizations of ylr(x) are generated by both (i) randomly shuffling temporal sequence, and (ii) adding pseudo-Gaussian-distributed noise to each surrogate point in proportion to the corresponding value of point uncertainty (i.e., replicate SEM, for example). In this way, specifically accounted for in the surrogate realizations are both (i) the influence of temporal patterning, and (ii) the magnitude of point-wise experimental uncertainty. Then, as with the original ylr(x) sequence, optimal values of ALPHA and BETA are determined, along with a corresponding CHI2, and retained in memory for each surrogate at each test period/optimal phase. For each test period/optimal phase are then calculated the mean and standard deviation of the surrogate BETA values. These values, in relation to the BETA value obtained for the original ylr(x) series, are then used to calculate a one-sided significance probability based on a normality assumption, which, in fact, is satisfied by the distribution of BETA values obtained from the 1000 randomized surrogates. A summary of the analytical session is then produced for each time series, composed of entries for only those test periods that correspond to CHI2 minima.

In the LD yw head time course, COSOPT scored 121 genes as cycling with p<0.01 (Table 1). This result likely is an underestimate of the total number of cycling genes, as previously characterized clock components such as per (which cycles with p=0.015) and clk (p=0.03) fall outside of this category. Since each individual cycling gene could not be confirmed, the very conservative p value criterion was used to select clock-controlled genes for further study.

TABLE 1

COSOPT assigned a p value to each putative cycling gene*

| | Cycling genes p < 0.01 | p < 0.025 | p < 0.05 |
|---|---|---|---|
| Heads | 120 | 478 | 1206 |
| Bodies | 177 | 524 | 1144 |

*see Young and Kay, supra, 2001.

Cycling genes were grouped in clusters according to the phase of peak expression. The phase distribution is shown in Ceriani et al., supra, 2002 (see FIG. 1A, demonstrating that output genes peak at different times in fly heads and bodies. Genes were grouped according to the phase calculated by COSOPT; each cluster represents genes peaking at the specified time ±2 hr. ZT0 ("Zeitgeber Time 0") refers to the time when lights are switched on. Genes are expressed as percentage of the total number of cycling ones.) Clock-controlled genes peak at all times during the day. More than 100 genes were identified by COSOPT as cycling with a p<0.01 in the head time course, and were plotted according to the peak of expression. A detailed list of cycling genes and corresponding phases can be found in Table 2).

This approach allowed the identification of several novel phases of peak expression (ZT4, ZT8, ZT12), and allowed a direct comparison between the different genes within the same experiment. All phases were similarly represented with the exception of ZT 8, where a larger proportion of the genes appeared to reach maximum levels. This result is in contrast to those reported for *Arabidopsis* (Harmer et al., supra, 2000) and cyanobacteria (Golden et al., *Ann. Rev. Plant Physiol. Plant Mol. Biol.* 48:327, 1997). Internal validation of this approach towards the identification of novel output genes came from the observation that previously characterized cyclers such as per, tim, vri, to, and even low amplitude genes such as clk and cry, displayed a circadian pattern in gene expression in the expression array experiment.

To confirm the circadian nature of the newly identified target genes, an independent experiment under free-running conditions was performed. One of the hallmarks of clock-controlled activity is the persistence of the rhythms in the absence of

TABLE 2

Cycling genes in fly heads (p < 0.01) are categorized by known or predicted function. Gene ID lists either the gene name (if known) or the Celera Transcript (CT) number, as well as the associated p value and phase under entrained (LD) and free running (DD) conditions.

| | | LD experiment | | DD experiment | |
|---|---|---|---|---|---|
| Gene ID | Function | p-Beta | Phase | pBeta | Phase |
| | CELL ADHESION | | | | |
| CT35785 | | 8.27E−03 | 21.3 | | |
| Tm | tartan | 7.68E−03 | 9.7 | | |
| | METABOLISM | | | | |
| CT1116 | succinyl CoA transferase | 4.64E−03 | 4.2 | | |
| CT22171 | isocitrate dehydrogenase (NADP+) | 4.59E−03 | 20.6 | 2.35E−01 | 21.1 |
| CT34968 | 3-OH isobutyrate dehydrogenase | 4.19E−03 | 3.2 | 3.07E−02 | 2.5 |
| CT12987 | short-branched chain acyl CoA dehydrogenase | 4.77E−03 | 0.5 | 9.06E−02 | 21.1 |
| CT41571 | aldehyde dehydrogenase | 9.50E−03 | 18.5 | 8.40E−02 | 22.0 |
| CT1187 | choline phosphate cytidil transferase | 9.92E−03 | 8.8 | 2.30E−02 | 8.8 |
| CT11757 | anon 23-Da | 4.04E−03 | 14.6 | | |
| Hmgs | hydroxymethylglutaryl-CoA synthase | 6.87E−03 | 21.6 | | |
| CT16527 | cholesterol O acyl transferase | 8.02E−03 | 7.8 | | |
| CT40163 | Angiotensin-converting enzyme | 2.26E−03 | 13.4 | | |
| CT12411 | oxido reductase | 7.54E−03 | 8.4 | | |
| | DEVELOPMENT | | | | |
| CT27880 | yellow-d2 | 5.51E−03 | 8.8 | 4.96E−03 | 15.0 |
| Idgf1 | Imaginal Disc Growth Factor 1 | 6.02E−03 | 20.7 | | |
| mbc | myoblast city | 5.04E−03 | 11.7 | | |
| | DETOXIFICATION | | | | |
| cyp6a21 | Cytochrome P450 6a21 | 3.84E−03 | 21.2 | 6.82E−03 | 2.2 |
| Ugt35b | UDP-glycosyltransferase 35b | 4.04E−03 | 3.7 | 9.80E−03 | 3.0 |
| CT38753 | gluthathione S-transferase | 4.95E−03 | 5.6 | | |
| CT38747 | gluthathione S-transferase | 7.51E−03 | 5.1 | | |
| cyp4e3 | Cytochrome P450 4e3 | 3.30E−03 | 9.0 | 6.41E−03 | 14.2 |
| cyp6d5 | Cytochrome P450 6d5 | 6.05E−03 | 21.6 | | |
| cyp6a17 | Cylochrome P450 6a17 | 9.37E−03 | 2.9 | | |
| CT16545 | glutathione transferase | 2.92E−03 | 7.8 | 1.58E−01 | 2.9 |
| cyp6a2 | Cytochrome P450 6a2 | 3.06E−03 | 7.9 | 1.49E−02 | 13.0 |
| cyp18 | Cytochrome P450 18 | 6.87E−03 | 17.1 | 6.86E−03 | 15.7 |
| | HEME METABOLISM | | | | |
| Alas | 5-Aminolevulinate synthase | 9.99E−03 | 22.5 | | |
| CT34507 | heme oxygenase-like | 8.79E−03 | 9.1 | 1.28E−02 | 14.2 |

TABLE 2-continued

Cycling genes in fly heads (p < 0.01) are categorized by known or predicted function. Gene ID lists either the gene name (if known) or the Celera Transcript (CT) number, as well as the associated p value and phase under entrained (LD) and free running (DD) conditions.

| | | LD experiment | | DD experiment | |
|---|---|---|---|---|---|
| Gene ID | Function | p-Beta | Phase | pBeta | Phase |
| | LIGAND BINDING/CARRIER | | | | |
| CT6764 | glucan alfa 1,4 glucosidase | 4.20E−03 | 18.4 | 9.98E−02 | 22.5 |
| glob1 | globin 1 | 6.68E−03 | 20.1 | 1.22E−01 | 21.2 |
| CT33362 | | 7.58E−03 | 20.4 | 2.36E−02 | 22.0 |
| CT28495 | | 2.79E−03 | 13.9 | 2.94E−02 | 21.9 |
| | NEUROTRANSMISSION | | | | |
| ple | tyrosine 3-monooxygenase | 4.52E−03 | 2.4 | 6.62E−03 | 1.6 |
| Eaat2 | Excitatory amino acid transporter 2 | 4.36E−03 | 13.2 | | |
| Dat | Dopamine N acetyltransferase | 5.18E−03 | 9.5 | | |
| CT42497 | glycine transporter | 5.64E−03 | 6.9 | 5.77E−03 | 13.1 |
| b | black, glutamate decarboxylase | 7.66E−03 | 16.2 | | |
| | PHOTORECEPTOR | | | | |
| Cry | Cryptochrome | 3.65E−03 | 1.1 | | |
| | PROTEASE INHIBITORS | | | | |
| serpin | serine protease inhibitor | 8.34E−03 | 20.0 | | |
| CT37177 | | 9.29E−03 | 14.6 | | |
| CT37195 | | 8.24E−03 | 10.4 | | |
| | PROTEIN SYNTHESIS/DEGRADATION | | | | |
| CT18196 | ubiquitin thiolesterase | 2.23E−03 | 13.1 | 7.31E−04 | 16.5 |
| pros26 | proteasome 26 kDa protein | 4.89E−03 | 8.7 | 1.69E−02 | 8.4 |
| pros26.4 | Proteasome 26S subunit subunit 4 ATPase | 7.14E−03 | 7.9 | | |
| CT28749 | 26 S proteasome regulatory subunit p39A | 6.22E−03 | 8.9 | 1.44E−02 | 10.7 |
| CT7240 | translation initiation factor (eIF-5) | 7.44E−03 | 8.5 | 2.91E−02 | 9.5 |
| CT39962 | tRNA synthase | 6.46E−03 | 20.8 | | |
| | PROTEIN FOLDING | | | | |
| CT16169 | heat shock protein 27-like | 7.44E−03 | 21.9 | | |
| Cnx99A | Calnexin 99A | 2.81E−03 | 17.4 | 6.61E−02 | 19.2 |
| | TRANSCRIPTION | | | | |
| CT30663 | | 6.96E−03 | 11.6 | | |
| tim | Timeless | 4.66E−03 | 16.4 | 4.58E−03 | 17.4 |
| Mad | Mothers against dpp | 4.97E−03 | 14.5 | | |
| vri | Vrille | 5.47E−03 | 13.6 | 1.58E−03 | 15.4 |
| CT31519 | | 5.08E−03 | 2.8 | 3.43E−01 | 7.5 |
| CT19628 | | 6.28E−03 | 16.6 | | |
| CT17296 | | 4.78E−03 | 14.1 | 1.11E−02 | 17.4 |
| CT18631 | TfII A-L | 8.42E−03 | 9.3 | | |
| 140up | upstream of RpII14 | 9.13E−03 | 17.5 | 9.15E−02 | 15.4 |
| | SIGNAL TRANSDUCTION | | | | |
| Akap200 | protein kinase A anchoring protein | 6.23E−03 | 15.6 | | |
| Pk61C | Protein kinase 61C | 2.92E−03 | 10.8 | 2.32E−02 | 14.1 |
| Pka-C3 | ser/thr kinase | 4.85E−03 | 15.3 | 5.66E−02 | 7.6 |
| CT35755 | | 9.09E−03 | 21.5 | 1.93E−01 | 4.4 |
| CT27512 | Ras small monomeric GTPase | 8.14E−03 | 9.3 | 1.16E−03 | 12.4 |
| Slob | Slowpoke binding protein | 3.04E−03 | 18.0 | 2.21E−03 | 16.3 |
| CT34849 | Chd64 | 9.76E−03 | 5.5 | | |
| | STRESS RESPONSE | | | | |
| CT25938 | superoxide dismutase (Cu—Zn) | 3.26E−03 | 8.6 | | |
| Hsp22 | Heat shock protein 22 | 7.82E−03 | 17.6 | | |
| to | Takeout | 8.26E−03 | 21.7 | 5.34E−02 | 2.1 |
| | STRUCTURAL PROTEINS | | | | |
| dlp | heparin sulfate proteoglycan | 7.39E−03 | 11.2 | | |
| Sulf1 | N-acetylglucosamine-6-sultase | 8.98E−03 | 8.8 | 1.26E−02 | 9.4 |
| betaTub56D | beta Tubulin56D | 8.71E−03 | 10.0 | 1.45E−01 | 22.9 |
| CT31310 | | 8.92E−03 | 6.2 | | |
| CT31613 | Thrombospondin | 2.25E−03 | 10.3 | 2.38E−02 | 11.9 |
| CT15377 | | 9.13E−03 | 5.2 | 2.29E−02 | 3.0 |
| Cpn | Calphotin | 8.94E−03 | 7.2 | 2.98E−02 | 9.9 |
| capu | cappuccino | 9.98E−03 | 18.5 | | |

TABLE 2-continued

Cycling genes in fly heads (p < 0.01) are categorized by known or predicted function. Gene ID lists either the gene name (if known) or the Celera Transcript (CT) number, as well as the associated p value and phase under entrained (LD) and free running (DD) conditions.

| Gene ID | Function | LD experiment | | DD experiment | |
|---|---|---|---|---|---|
| | | p-Beta | Phase | pBeta | Phase |
| | TRANSPORTERS | | | | |
| CT42567 | high affinity inorganic phosphate:sodium transporter | 3.83E-03 | 0.2 | 4.57E-02 | 22.9 |
| CT30701 | glucose transporter | 8.23E-03 | 7.7 | | |
| trpl | trp-like | 6.66E-03 | 9.8 | | |
| CT16777 | | 8.63E-03 | 8.6 | 1.31E-02 | 13.9 |
| | UNKNOWN FUNCTION | | | | |
| CT12588 | | 8.91E-03 | 23.5 | 2.87E-02 | 17.9 |
| CT31141 | | 9.90E-03 | 15.2 | | |
| CT28701 | | 7.65E-03 | 8.3 | | |
| CT34631 | | 8.27E-03 | 8.9 | | |
| CT6802 | | 7.37E-03 | 9.4 | | |
| CT32204 | | 3.85E-03 | 7.1 | 2.38E-03 | 7.7 |
| CT16557 | | 9.34E-03 | 8.8 | 2.14E-03 | 16.2 |
| CT16503 | | 7.86E-03 | 2.2 | 7.18E-03 | 4.9 |
| CT33900 | | 7.94E-03 | 18.9 | | |
| CT22515 | | 9.90E-03 | 14.1 | | |
| CT33647 | | 4.06E-03 | 1.0 | 7.49E-03 | 19.6 |
| CT18564 | | 9.89E-03 | 21.8 | | |
| CT25838 | | 5.23E-03 | 8.7 | | |
| CT30256 | | 8.04E-03 | 20.5 | | |
| CT33484 | | 3.57E-03 | 18.4 | 6.09E-03 | 21.0 |
| CT32008 | | 6.86E-03 | 8.3 | | |
| CT28709 | | 8.73E-03 | 7.9 | | |
| CT31865 | | 2.26E-03 | 9.2 | 1.23E-03 | 14.3 |
| CT32600 | | 7.94E-03 | 22.7 | 1.01E-02 | 22.0 |
| CT15908 | | 4.83E-03 | 8.8 | 2.40E-03 | 13.2 |
| CT32262 | | 2.32E-03 | 8.3 | 1.02E-03 | 10.2 |
| CT34135 | | 9.46E-03 | 5.5 | 7.15E-02 | 16.3 |
| CT34439 | | 9.64E-03 | 3.3 | 1.66E-01 | 15.7 |
| CT10556 | | 4.40E-03 | 8.7 | | |
| CT42539 | | 5.48E-03 | 8.5 | | |
| CT35916 | | 9.64E-03 | 5.9 | 1.14E-02 | 7.5 |
| CT33073 | | 4.59E-03 | 7.2 | 3.78E-03 | 10.0 |
| CT37044 | | 2.37E-03 | 20.6 | 6.98E-03 | 0.9 |
| CT29508 | | 8.79E-03 | 19.1 | 1.41E-01 | 1.3 |
| CT29612 | | 2.71E-03 | 19.5 | 3.37E-03 | 19.3 |
| CT35582 | | 2.66E-03 | 8.5 | 1.03E-03 | 14.4 |
| CT32596 | | 8.92E-03 | 10.8 | | |
| CT26517 | | 9.97E-03 | 4.8 | 3.09E-01 | 17.4 |
| CT29500 | | 4.71E-03 | 21.4 | 1.85E-02 | 2.3 |
| CT16351 | | 4.78E-03 | 15.5 | | |
| CT24597 | | 9.47E-03 | 4.5 | 2.78E-01 | 16.1 |
| CT26954 | | 9.35E-03 | 8.7 | | |
| CT25972 | | 8.46E-03 | 15.9 | | | environmental cues. Accordingly, the proportion of the novel outputs that showed reliable cycling profiles under constant darkness was determined. One of the limitations of this analysis under constant dark (DD) conditions is the "dampening" of the signal amplitude, which partially results from the desynchronization of individual cells in the absence of resetting environmental cues (Hardin, *Mol. Cell. Biol.* 14:7211, 1994). The data from both experiments are summarized in Table 2.

Circadian Transcriptional Regulation of Physiology

Although cyclic transcription is a signature of clock activity, important levels of regulation take place downstream. Several genes involved in various aspects of protein regulation were under rhythmic transcriptional control. Three genes were identified that cycle with a peak at ZT8 and are part of the 26S proteasome complex (see Ceriani et al., supra, 2002; FIG. 3A). pros26 encodes a multicatalytic endopeptidase that is part of the central 20S barrel-shaped structure (Saville and Belote, *Proc. Natl. Acad. Sci. USA* 90:8842, 1993). pros26.4 and rpn9 are part of the 19S regulatory complex, and correspond to the subunit 4 of the AAA-ATPase and the homolog of yeast rpn 9, which is required for assembly and stability of the proteasome, respectively. In *Drosophila*, different proteasome subunits are expressed throughout development, possibly to control specific processes such as cell division or morphogenesis (Haass and Kloetzel, *Exp. Cell Res.* 180:243, 1989). A putative de-ubiquitinating enzyme, the homolog of the mouse UBPY, with peak expression at ZT12 (see Ceriani et al., supra, 2002; FIG. 3A), also was identified. This cyclic pattern was confirmed independently by northern blot analysis. Northern blot analysis of independent head and body time courses confirmed the cyclic nature of the candidates tested and the timing of mRNA peaks (Suri et al., *EMBO J.* 18:675, 1999). "Gene ID", which refers to the cDNA used to probe the different time courses, had an expected peak time predicted by the array experiment, as follows: Gene ID CT 38753, ZT4; CT 8171, ZT4/8; CT 18196, ZT12; CT 33647, ZT20; CT 33647, ZT0; and CT12127, ZT8. De-ubiquitinating enzymes remove the polyubiquitin chain from conjugated proteins prior to their degradation by the proteasome. These enzymes can regulate degradation by the proteasome, or can be involved in ubiquitination processes not directing protein degradation, but rather subcellular localization. These results indicate that temporal regulation of the proteosome can be important in Drosophila physiology.

The observation that the expression of both the rate limiting enzyme on heme biosynthesis, d-aminolevulinate synthase (alas), and the rate limiting enzyme of heme degradation, heme oxygenase, cycle in Drosophila heads indicates that heme metabolism is tightly regulated by the clock (with a peak at ZT 20 and ZT8, respectively; see Ceriani et al., supra, 2002; FIG. 3B). Heme is involved in respiration, oxygen transport, detoxification, and signal transduction processes. However, as a chelator of iron, heme may promote deleterious cellular effects such as oxidative membrane damage. Thus, maintaining a proper balance between heme biosynthetic and degradation pathways is crucial for cellular homeostasis (Ryter and Tyrrell, *Free Rad. Biol Med.* 28:289, 2000).

In insects, P450 enzymes are thought to be involved in the biosynthetic pathways of ecdysteroids and juvenile hormones, and, as such, play a role in insect growth, development, and reproduction, as well as metabolize natural plant products and insecticides, resulting in bioactivation or detoxification (Feyereisen, *Ann. Rev. Entomol.* 44:507, 1999). The present study revealed 6 different cytochrome P450 genes, cyp4e3, cyp6a2, cyp6a17, cyp6a21, cyp6d5, and cyp18 cycle with different phases (ZT 8, 4, 0, 20, and 16, respectively; see Ceriani et al., supra, 2002; FIG. 3C). The only functionally characterized enzyme thus far is cyp6a2, which is involved in the metabolism of organophosphorus insecticides. Detoxification often occurs in two phases. The initial compound can be transformed into a more reactive species (usually via redox reactions catalyzed by cytochrome P450 enzymes); in the second phase, highly polar groups such as UDP-glucuronosyl or glutathione are added either to the products of the first phase or, in some cases, directly to the toxic chemicals. The enzymes involved in this second stage phase include UDP-glucuronosyl transferases (ugt) and gluthathione S-transferases (GST's). Products of phase II are highly hydrophilic, can no longer cross membranes, and are eliminated by secretion. The present study revealed that ugt35b and several GST's also cycle in fly heads (see Ceriani et al., supra, 2002; FIG. 3D), indicating that multiple steps in the biotransformation process are under circadian control.

Another gene that was under circadian control is ple, indicating that neurotransmission is a clock-controlled process. ple codes for the tyrosine 3-monooxygenase (also known as tyrosine hydroxylase), the first and rate limiting enzyme in dopamine biosynthesis. Dopamine is an intermediate in cuticular esclerotization and also functions as a signaling molecule in the fly nervous system. Dopamine can modulate certain forms of learning such as female sexual receptivity and habituation, as well as motor neuron activity and neuromuscular function in larva (Neckameyer, *Learn. Mem.* 5:157, 1998; Cooper and Neckameyer, *Comp. Biochem. Physiol. B.* *Biochem. Mol. Biol.* 122:199, 1999). The present studies revealed that ple is expressed at very low levels in fly heads, but cycles with high amplitude, peaking at ZT 4 under both entrained and free running conditions. ple expression falls below the level of detection in clk$^{jrk}$ (a mutation that impairs clock function; Allada et al., *Cell* 93:791, 1998). This result indicates that ple is a direct CLOCK target. ple represents one of the several examples of homolog genes cycling in both flies and mammals (Carre and Kay, *Plant Gene Research: Basic Knowledge and Application* (Dennis et al, Eds., 1995)).

The Clock Controls Different Sets of Genes in Different Tissues

To provide a more comprehensive view of clock control in a whole organism, cyclic gene expression was analyzed using male bodies as the source of total RNA, and compared these transcripts with those derived from heads. COSOPT identified 177 genes that cycled with a period between 20 and 28 hr ($p<0.01$; Table 3). As in the mouse, only a small proportion of cycling transcripts (12 genes) overlapped between the two tissues, including some previously identified clock components (such as tim, vri and cry). The analysis of the remaining genes revealed that a large number of genes that cycle solely in fly heads, nevertheless are expressed at medium to high levels in the bodies. The clock controls different subsets of genes in heads and bodies, with distributions observed of genes cycling in both tissues, cycling and expressed in only one, and expressed to mid-high levels in both but cycling in one. This result indicates that differential transcriptional regulation acts in this subset of clock outputs, in agreement to what has been found in the mouse (Carre and Kay, supra, 1995).

Potassium Channel as an Output of the Clock Involved in Sustained Rhythmic Behavior The identification of the clock-controlled genes allowed an investigation to identify those genes crucial for the control of rhythmic behavior. Among the candidates, slob (slowpoke binding protein) was identified. SLOB binds to the Ca2+-dependent voltage-gated potassium channel slowpoke (slo; Schopperle et al., supra, 1998), which, when mutated causes behavioral defects (Atkinson et al, *J. Neurosci.* 20:2988, 2000) and an altered mating song, also a hallmark of certain clock components (Peixoto and Hall, *Genetics* 148:827, 1998). SLOB has been shown to modulate SLO activity through the formation of a complex with a 14-3-3 protein, that is a downstream of several signaling pathways (Zhou et al., *Neuron* 22:809, 1999). In flight muscle, slowpoke functions in action potential repolarization (Elkins et al., *Proc. Natl. Acad. Sci. USA* 83:8415, 1986) and also was proposed to participate in the repolarization at the nerve terminal of the motoneurons (Gho and Mallart, *Pflugers Arch.* 407:526, 1986).

slob mRNA cycled robustly in fly heads in LD and DD (Table II; see Ceriani et al., supra, 2002; FIGS. 4A (entrained conditions) and 4B (free-running conditions)). This pattern is lost in the clk$^{jrk}$ mutant background, although it likely is not a direct CLK target because the overall levels of expression remain unchanged. In addition, slo mRNA oscillated in phase with slob in LD and DD; the level of expression was near the limit of detection of the technique (see Ceriani et al., supra, 2002; FIGS. 4A and 4B); slo cycling also was obliterated in the clk$^{jrk}$ mutant.

TABLE 3

List of cycling genes in fly bodies (p < 0.01), as in table II.

| Gene ID | Function | LD experiment p-Beta | Phase |
|---|---|---|---|
| DEFENSE/IMMUNITY | | | |
| CT8705 | peptidoglycan recognition protein | 1.87E−03 | 22.20 |
| Phas1 | eukaryotic-initiation-factor-4E binding protein | 9.76E−03 | 23.00 |
| Ag5r | Antigen 5-related | 2.10E−03 | 21.31 |
| Chit | chitinase-like | 6.84E−03 | 7.60 |
| CT5624 | chitinase-like | 3.01E−03 | 17.25 |
| CT30310 | | 9.84E−03 | 15.12 |
| CT29102 | | 3.51E−03 | 5.40 |
| CT16885 | PGRP-SC1b | 1.46E−03 | 8.50 |
| DEVELOPMENT | | | |
| Idgf4 | Imaginal Disc Growth Factor 4 | 2.20E−03 | 3.20 |
| CT13185 | dorso-ventral patterning in oogenesis | 8.53E−03 | 4.90 |
| DETOXIFICATION | | | |
| cyp9b2 | | 4.91E−03 | 4.70 |
| CT20826 | cyp18a1 | 4.07E−03 | 19.34 |
| Cyp6gl | | 1.86E−03 | 8.03 |
| CT38747 | glutathione transferase | 2.29E−03 | 5.90 |
| GstD1 | glutathione S transferase B1 | 5.67E−03 | 7.30 |
| CT35150 | glutathione S-transferase-like | 4.46E−03 | 7.50 |
| CT35071 | UDP-glucuronosyltransferase | 9.59E−03 | 4.90 |
| ELECTRON TRANSFER | | | |
| Cyt-A5 | Cytochrome A5-related | 7.50E−03 | 7.90 |
| LIGAND BINDING/CARRIER | | | |
| CT3751 | triglyceride binding | 6.09E−03 | 6.50 |
| Mp20 | Muscle protein 2 | 8.59E−03 | 18.85 |
| Dbi | Diazepam-binding inhibitor | 7.95E−03 | 8.60 |
| PebIII | ejaculatory bulb protein III | 4.14E−03 | 19.62 |
| CT33980 | neural Lazarillo | 9.36E−03 | 19.72 |
| CT31326 | antennal binding protein X-like | 6.24E−03 | 3.90 |
| CT32778 | Odorant binding protein | 2.78E−03 | 5.40 |
| CT21061 | fatty acid binding protein-like | 1.94E−03 | 9.00 |
| METABOLISM | | | |
| CT41369 | | 2.57E−03 | 4.70 |
| Wun | phosphatidate phosphatase | 6.99E−03 | 19.01 |
| LysX | Lysozyme X | 9.50E−03 | 17.55 |
| CT16187 | 3-hydroxyisobutyryl-CoA hydrolase | 6.41E−03 | 0.50 |
| CT24308 | threonine dehydratase | 6.48E−03 | 7.90 |
| CT6492 | maltase L-like | 2.28E−03 | 6.80 |
| Hmgs | hydroxymethylglutaryl-CoA synthase | 6.40E−03 | 23.06 |
| LvpH | larval visceral protein H | 4.80E−03 | 7.50 |
| Pepck | Phosphoenolpyruvate carboxykinase | 6.50E−03 | 11.00 |
| Scu | 3-hydroxyacyl-CoA dehydrogenase | 9.57E−03 | 8.90 |
| CT17038 | malate dehydrogenase | 3.07E−03 | 8.10 |
| CT36683 | alpha-Amylase-like | 1.74E−03 | 8.40 |
| CT6532 | maltase H-like | 4.49E−03 | 7.30 |
| CT22063 | triacylglycerol lipase-like | 9.88E−03 | 7.60 |
| CT22069 | hexokinase | 2.84E−03 | 8.00 |
| CT21171 | carbonate dehydratase-like | 6.81E−03 | 4.70 |
| CT12913 | ubiquinone biosynthesis | 6.51E−03 | 21.39 |
| CT34308 | UDP-glucose epimerase | 5.17E−03 | 8.50 |
| CT18319 | pyrroline 5-carboxylate reductase-like | 6.39E−03 | 7.30 |
| CT33098 | alpha-glucosidase II | 3.93E−03 | 7.40 |
| CT19053 | carbonate dehydratase-like | 5.82E−03 | 16.25 |
| CT28913 | glucosylceramidase-like | 7.84E−03 | 9.45 |
| RfaBp | retinoid- and fatty-acid binding protein | 2.28E−03 | 8.40 |
| CT26924 | glucose dehydrogenase-like | 6.49E−03 | 7.50 |
| alpha-Est5 | carboxylesterase | 8.47E−03 | 10.00 |
| RfaBp | retinoid- and fatty-acid binding protein | 1.50E−03 | 9.60 |
| Pug | formate--tetrahydrofolate ligase | 8.23E−03 | 7.60 |
| Lectin-galC1 | Galactose-specific C-type lectin | 3.60E−03 | 9.00 |
| alpha-Est7 | alpha-Esterase-7 | 9.35E−03 | 9.70 |
| ade5 | phosphoribosylaminoimidazole carboxylase; EC:4.1.1.21 | 3.38E−03 | 9.50 |
| Pdh | photoreceptor dehydrogenase | 9.23E−03 | 6.90 |
| CT30991 | IMP cyclohydrolase | 4.38E−03 | 9.80 |
| CT24026 | alpha-galactosidase | 7.24E−03 | 8.90 |
| CT9666 | transaldolase | 3.14E−03 | 8.50 |
| CT39259 | oxidoreductase | 3.46E−03 | 3.10 |

TABLE 3-continued

List of cycling genes in fly bodies (p < 0.01), as in table II.

| Gene ID | Function | LD experiment p-Beta | Phase |
|---|---|---|---|
| CT41283 | cholinephosphate cytidylyltransferase | 6.56E−03 | 0.42 |
| RfaBp | retinoid- and fatty-acid binding protein | 1.50E−03 | 9.60 |
| Pug | formate--tetrahydrofolate ligase | 8.23E−03 | 7.60 |
| Lectin-galC1 | Galactose-specific C-type lectin | 3.60E−03 | 9.00 |
| CT33239 | N-acetyl transferase | 9.11E−03 | 15.44 |
| CT31087 | rRNA methyltransferase | 4.32E−03 | 13.20 |
| CT34977 | epoxide hydrolase | 5.71E−03 | 6.30 |
| MUSCLE CONTRACTION | | | |
| Mhc | myosin II heavy chain | 6.81E−03 | 17.56 |
| TpnC73F | Troponin C at 73 F | 6.66E−03 | 17.79 |
| PROTEASES | | | |
| CT15463 | zinc carboxypeptidase | 7.73E−03 | 21.92 |
| CT14806 | vitellogenic carboxypeptidase | 7.54E−03 | 6.80 |
| CT14378 | carboxypeptidase-like (inactive) | 3.89E−03 | 1.50 |
| CT4209 | chymotrypsin | 3.30E−03 | 22.58 |
| CT37183 | serine protease inhibitor | 1.66E−03 | 9.00 |
| CT25448 | chymotrypsin | 8.12E−03 | 21.11 |
| CT8699 | serine protease-like | 7.10E−03 | 22.52 |
| CT19724 | serine protease | 6.97E−03 | 20.04 |
| CT37173 | serine protease-like | 1.98E−03 | 14.30 |
| CT3996 | cathepsin | 4.41E−03 | 9.30 |
| CT20780 | cathepsin L | 5.44E−03 | 13.40 |
| Ser99Da | Serine protease 1 | 9.03E−03 | 23.59 |
| Ser99Db | Serine protease 2 | 9.91E−03 | 23.18 |
| CT29408 | serine protease | 4.45E−03 | 22.77 |
| gammaTry | gammaTrypsin | 2.77E−03 | 20.66 |
| PROTEIN SYNTHESIVE/FOLDING | | | |
| CT25442 | ribosomal protein K11-like | 7.71E−03 | 20.20 |
| CT17486 | chaperone | 2.69E−03 | 19.57 |
| SIGNAL TRANSDUCTION | | | |
| Pp1-13C | ser/thr phosphatase | 9.91E−03 | 5.80 |
| CkIIbeta | casein kinase II beta subunit | 7.15E−03 | 16.77 |
| Cry | cryptochrome | 5.77E−03 | 4.10 |
| Lk6 | heat shock construct of Kidd | 4.74E−03 | 5.20 |
| CT22109 | Accessory gland peptide 36DE | 9.84E−03 | 17.93 |
| STRESS RESPONSE | | | |
| Cat | Catalase | 1.53E−03 | 8.80 |
| CT33074 | takeout | 4.71E−03 | 0.65 |
| CT9894 | heat shock protein 70 | 6.26E−03 | 23.78 |
| STRUCTURAL PROTEINS | | | |
| Gel | Gelsolin | 6.95E−03 | 7.80 |
| Msp-300 | Muscle-specific protein 3 | 8.02E−03 | 16.42 |
| CT33880 | cuticle protein-like | 9.68E−03 | 17.33 |
| Glt | Glutactin | 4.72E−03 | 9.10 |
| CT41348 | A-band-protein-225 | 6.88E−03 | 17.09 |
| TRANSCRIPTION | | | |
| CT15944 | | 7.39E−03 | 17.21 |
| CT6009 | | 9.47E−03 | 13.50 |
| Tim | timeless | 3.98E−03 | 17.53 |
| TRANSPORTER | | | |
| Vha13 | hydrogen-transporting two-sector ATPase | 6.26E−03 | 21.66 |
| BY8473 | ATP-binding cassette transporter | 1.48E−03 | 22.77 |
| CT27832 | sodium/phosphate cotransporter | 4.17E−03 | 17.16 |
| CT13124 | zetaCOP | 5.41E−03 | 20.56 |
| CT14766 | ATP-binding cassette transporter | 9.08E−03 | 18.53 |
| CT30783 | sugar transporter-like | 6.99E−03 | 8.00 |
| CT10168 | sodium/phosphate cotransporter | 6.97E−03 | 18.12 |
| CT19169 | sugar transporter | 6.06E−03 | 6.70 |
| CT33284 | | 4.70E−03 | 8.90 |
| CT15971 | amino-acid permeas-like | 9.52E−03 | 17.98 |
| UNKNOWN FUNCTION | | | |
| CT19307 | | 7.73E−03 | 20.48 |
| CT21613 | | 8.81E−03 | 17.97 |
| CT35864 | | 9.38E−03 | 14.41 |

TABLE 3-continued

List of cycling genes in fly bodies (p < 0.01), as in table II.

| Gene ID | Function | LD experiment p-Beta | Phase |
|---|---|---|---|
| CT14230 | | 6.06E−03 | 6.50 |
| CT14296 | | 2.49E−03 | 6.60 |
| CT23898 | | 2.59E−03 | 9.30 |
| CT23894 | | 8.82E−04 | 7.50 |
| CT21019 | | 7.01E−03 | 5.70 |
| CT9093 | | 8.76E−03 | 18.52 |
| Mst57Dc | Male-specific RNA 57Dc | 6.37E−03 | 16.93 |
| Gip | Gip-like | 8.12E−03 | 9.80 |
| CT35241 | | 6.39E−03 | 9.30 |
| CT25774 | | 7.17E−03 | 8.00 |
| CT27394 | | 3.05E−03 | 9.00 |
| CT35953 | | 8.23E−03 | 3.00 |
| CT34370 | | 9.41E−03 | 17.70 |
| CT22505 | | 6.20E−03 | 7.60 |
| CT12127 | | 1.59E−03 | 7.70 |
| CT35796 | | 5.00E−03 | 17.12 |
| CT26922 | | 4.52E−03 | 8.90 |
| CT33647 | | 3.27E−03 | 0.00 |
| CT27834 | | 2.31E−03 | 7.80 |
| CT18564 | | 2.24E−03 | 23.50 |
| CT35055 | | 8.36E−03 | 7.50 |
| CT35089 | | 9.38E−03 | 5.00 |
| CT8227 | | 5.83E−03 | 20.29 |
| CT18118 | | 9.50E−03 | 20.02 |
| CT42569 | | 1.54E−03 | 22.14 |
| CT40493 | | 9.81E−03 | 9.00 |
| CT33419 | | 9.49E−03 | 1.95 |
| CT34875 | | 9.46E−03 | 15.36 |
| CT32604 | | 9.65E−03 | 19.09 |
| CT39634 | | 6.22E−03 | 8.40 |
| CT22395 | | 5.73E−03 | 21.98 |
| CT33153 | | 8.49E−03 | 5.20 |
| CT12789 | | 5.68E−03 | 21.28 |
| CT1789 | | 6.56E−03 | 2.80 |
| CT40966 | | 7.27E−03 | 6.00 |
| CT36877 | | 6.76E−03 | 23.39 |
| CT26804 | | 3.60E−03 | 21.31 |
| CT26802 | | 4.05E−03 | 21.61 |
| CT28427 | | 2.07E−03 | 5.40 |
| CT38785 | | 9.84E−03 | 2.50 |
| CT34717 | | 4.17E−03 | 5.70 |
| CT18134 | | 3.68E−03 | 9.90 |
| CT33073 | | 5.64E−03 | 13.90 |
| CT37044 | | 4.08E−03 | 3.30 |
| CT33083 | | 8.21E−03 | 9.30 |
| CT29612 | | 9.10E−03 | 20.14 |
| CT20261 | | 4.25E−03 | 7.80 |
| CT34939 | | 1.41E−03 | 9.40 |
| CT34936 | | 8.21E−03 | 11.00 |
| CT37419 | | 8.18E−03 | 13.90 |
| CT36793 | | 3.98E−03 | 16.56 |
| CT18390 | | 3.53E−03 | 1.30 |
| CT9987 | | 9.65E−03 | 7.70 |
| CT29500 | | 4.76E−03 | 21.63 |
| CT26166 | kisir | 4.69E−03 | 21.50 |
| CT35842 | | 6.17E−03 | 8.60 |
| CT32316 | | 7.80E−03 | 3.40 |
| CT16297 | | 9.32E−03 | 17.56 |
| CT21565 | | 9.20E−03 | 18.83 |
| CT42272 | | 5.07E−03 | 6.20 |
| CT39472 | Peritrophin-15a | 4.86E−03 | 20.12 |
| C122723 | Senescence marker protein-3 | 3.39E−03 | 8.90 |

To validate the cycling of slo at the protein level, SLO protein abundance was determined in light/dark cycles in fly head extracts by western blot analysis. Time courses were performed as described above. About 10 µl of wild type and mutant fly heads were loaded into precast 4-15% acrylamide gels (BioRad). Gels were transferred in 15% methanol TRIS-glycine buffer onto MSI supported nitrocellulose. Primary antibodies used were rabbit IgG anti-SLO (1:500) and mouse monoclonal IgG anti-hsp70 (1:2000, Sigma). Washes were performed in TBS (for SLO) or TBS 0.5% TWEEN detergent (for hsp70). Appropriate secondary antibodies were detected using ECF (Amersham). The results revealed that SLO oscillated with a peak at ZT20 (Ceriani et al., supra, 2002; FIG. 4C).

In *Drosophila*, a considerable body of work identified a small group of cells called ventral lateral neurons (LNv) as the pacemaker neurons. The LNv's play a major role in the control of circadian locomotor activity under entrained and free running conditions (Helfrich-Förster, *J. Comp. Physiol.* (*A*) 182:435, 1998). Although slo expression pattern has been studied extensively (Becker et al., *J. Neurosci.* 15:6250, 1995), little is known about its expression in the regions of the brain relevant to circadian control of behavior. To further characterize the role of slowpoke as an output of the clock, SLO spatial distribution was examined in the fly head. Anti-SLO histochemistry was performed using CNS whole mounts. Wild-type (Canton-S) flies were subjected to at least 3 cycles of 12 hr:12 hr light:dark. Males were sacrificed between ZT 18-20 and their brains dissected in 1×PBS. The specimens were fixed in 4% paraformaldehyde for 30-60 min at room temperature, with gentle shaking. Tissues were washed 3 times with 0.2 M phosphate; then washed 3 further times in TNT (0.1M Tris HCl/0.3M NaCl (pH 7.4), 0.5% TRITON X-100 detergent); the duration of each wash was 20 min. The washed specimens were preincubated in a blocking solution, composed of 4% normal donkey serum (diluted in TNT) for 2-3 hr.

Anti-SLO antibody was applied at a dilution of 1:100 directly in the blocking solution and incubated overnight at 10-12° C. with gentle shaking. The tissues were then washed 6 times (20 min each) in TNT and subsequently incubated with Cy TM 5-conjugated secondary anti-rabbit IgG at dilution of 1:200 (Jackson ImmunoResearch; West Grove Pa.) for 2 hr at room temperature. All further steps were performed in the dark: Tissues were washed 3 times in TNT, followed by 3 times in 0.1M phosphate buffer (6 washes; 20 min each). Brains were then mounted with 2% n-propyl gallate (80% glycerol in 0.2 M phosphate buffer, pH 7.4). Samples were observed using an MRC600 laser-scanning confocal microscope (BioRad, Richmond, Calif.).

Immunocytochemistry analysis on whole mount brain preparations indicated that this channel is expressed in a subset of the LNv. Images were produced by collecting numerous Z series sections (approx. 2 μm each) then projecting them into one figure, which represents approximately 40 μm of confocal stacking. Eighteen brains were processed in this manner; and in 16 of the specimens, prominent signals appeared in certain bilaterally symmetrical cell clusters which are located near the anterior rim of the medulla optic lobe. These cells appeared to be either a subset of the clock-gene expressing Lateral Neurons (LNs) or near their locations. SLO immunoreactivity within these putative LNs appeared to be cytoplasmic. Additional anti-SLO-mediated staining was detected less frequently. Signals were detected near the Kenyon cells of the mushroom bodies (in a medial region of the dorsal brain), which were weak compared with the putative LN staining and observed in only 50% of the brains. In the majority of the specimens, relatively strong signals appeared at the edges of the optic lobes, and within those ganglia scattered, weak signals were erratically observed.

Prompted by evidence that SLO was involved in mediating locomotor activity, the locomotor activity in two slo mutants, slo1 and slo4, was examined. slo1 was generated by EMS mutagenesis and slo4 by gamma irradiation; the latter is a result of an inversion that deletes the promoters required for specific expression in neural and muscle tissue. Wild type flies showed increased locomotor activity near dawn and dusk, and remained quiescent the rest of the day (see Ceriani et al., supra, 2002; FIGS. 5 and 6; see, also, Hamblen-Coyle et al., *J. Insect Behav.* 5:417, 1992). Furthermore, the bursts of activity did not merely follow the next environmental transition, but, instead, anticipated the transition. These so called "startle effects" remained in some of the mutants affecting core clock components when the flies were kept under entrained conditions (such as per$^o$), making them appear rhythmic. Interestingly, norpA/per$^o$ double mutants also displayed startle effects, indicating that this effect is not mediated by light through the visual pathway (Wheeler et al., *J. Biol. Rhythms* 8:67, 1993).

FIG. 5 of Ceriani et al. (supra, 2002) shows representative individual of wild type CS and yw flies (left), and the mutants slo1, slo4, per$^o$ and clk$^{jrk}$. Flies were entrained for 5 days before the onset of the experiment. During the experiments flies were kept in LD for 3-4 days, then switched to DD and monitored for at least another week. Rhythmicity and total activity in LD and DD conditions was determined using the Clocklab™ software package. Newly enclosed flies were entrained to 12 hr: 12 hr LD cycles for 3 days, and adult males were placed in glass tubes and monitored for activity with infrared detectors and a computerized data collection system (Trikinetics, MA). Activity was monitored in LD conditions for 3 to 4 days, when the flies were released into constant darkness (DD) at least for a week. Data was analyzed using Clocklab/Matlab software package. Only those flies that were alive 2 days after the analysis ended were taken into account. Periodogram analysis of flies that were scored as arrhythmic in Table IV produced no strong peak that was statistically significant with p<0.001. Overall activity was calculated by averaging equivalent bins during LD or DD cycles for each fly, then taking an average of all the flies within each genotype.

Wild type CS and yw were rhythmic in LD and in DD, where the endogenous period became apparent (see Ceriani et al., supra, 2002; FIG. 5; Table 4). per$^o$ and clk$^{jrk}$ mutants, which have defects in core clock components, behaved differently under entrained conditions; per$^o$ flies remained mostly rhythmic in LD, whereas clk$^{jrk}$ often were not (see above). slo1 and slo4 mutants were arrhythmic in LD, although the strength of the phenotype varied with the mutation. The lack of rhythmicity persisted under free running conditions (Ceriani et al., supra, 2002; FIG. 5; Table IV).

TABLE 4

A null mutation in the slowpoke potassium channel does not change the overall activity levels

| Genotype (n) | Rhythmic lines (%) | | Activity (total counts/day) | |
| --- | --- | --- | --- | --- |
| | LD | DD | LD | DD |
| CS (53) | 100 | 100 | 1017 | 1204 |
| yw (74) | 86 | 88 | 611 | 910 |
| slo4 (68) | 1 | 1 | 810 | 813 |
| slo1 (41) | 29 | 54 | 808 | 820 |
| clk$^{jrk}$ (41) | 22 | 7 | 1110 | 1518 |
| per$^o$ (35) | 71 | 3 | 695 | 1141 |

Number of flies analyzed within each genotype is expressed in parentheses.

Several scenarios can account for these observations. A mutation in slowpoke can cause arrhythmicity if it directly affects the output pathway controlling behavior, i.e., affecting the excitability of the motor neurons that control behavior. Alternatively, the mutation can act at the level of the pacemaker neurons by reducing the coupling between the LNs, which also can cause the observed lack of behavioral rhythmicity. Slowpoke also can "gate" (McWatters et al., *Nature*

408:716, 2000) fly locomotor activity that would be regulated by additional unidentified components.

To determine if this mutation caused general sluggishness, which could per se result in arrhythmicity, the total activity displayed by the different genotypes under LD and DD conditions was quantified. Wild type flies were slightly more active under constant darkness, but both slo mutants responded the same in both environmental conditions. More importantly, the overall levels of activity were not different from those of the wild type flies (Table 4). When the actograms of wild type and slo4 mutant flies were superimposed, these average activity plots revealed features that were not apparent when inspecting individual flies. The most striking difference was the lack of anticipation and response to the transitions (startle effect) in the slo4 flies (see Ceriani et al., supra, 2002; FIG. 6, showing average activity plots for wild type and slo4 mutant flies; activity records of the LD portion of the experiment for 53 wild type flies and 28 slo4 flies were used for the analysis; to superimpose the separate animal records the levels of activity were normalized per fly per day). This result indicates that the gating that consolidates behavior around dawn and dusk was missing in the slo4 flies.

In summary, steady state mRNA levels were examined using high density oligonucleotide arrays for circadian patterns of expression in the fly head and body. This analysis identified several genes that are known to be rhythmically expressed, as well as several hundred genes of known and unknown function that also are under clock control. A number of aspects of fly physiology ranging from basic cellular metabolism to neurotransmission, stress resistance and detoxification were found to be under control of the biological clock. As in the mouse, few genes cycled in both heads and bodies, indicating that tissue specificity is an important component of circadian transcriptional regulation. Several cycling genes in the fly also cycled in the mouse, suggesting these gene are important output mediators or core clock components. Behavioral follow-up of one of genes, slo, indicates it is a central regulator of locomotor activity. The notion that a potassium channel is involved in the generation of rhythmic activity was proposed a number of years ago following the analysis of membrane conductance changes in isolated retinal neurons of the mollusk Bulla (McMahon and Block, *J. Comp. Physiol.* A161:335, 1987; Michel et al., *Science* 259:239, 1993). This observation, together with the finding that potassium currents are circadian regulated in the mouse, and that expression of Kcnma1, the slowpoke mouse ortholog, cycles (see Example 2), indicates that this mechanism of control of rhythmic activity is evolutionarily conserved, and utilized in more complex organisms.

EXAMPLE 2

Mammalian Circadian-Regulated Genes

Coordinate gene regulation can function to organize specific biological processes in a developmental, spatial, or temporal manner. The light dark cycle is an important temporal consideration as it influences many physiological processes in organisms ranging from cyanobacteria, fungi, plants, flies, mice, and humans (Young and Kay, *Nat. Rev. Genet.* 2:702, 2001). This temporal regulation is accomplished by a circadian clock, which, in mammals, resides in the suprachiasmatic nucleus (SCN) of the hypothalamus. In mammals, many important functions are under circadian control, including the sleep-wake cycle, hormonal rhythms, body temperature, and feeding. Powerful *Drosophila* and mammalian genetics have implicated PAS (Per-Arnt-Sim) domain-containing transcription factors in the regulation of clock gene expression (Dunlap, *Cell* 96:271, 1999). Characterization of several of these factors has revealed a feedback inhibitory loop that governs transcriptional rhythmicity with a period of 24 hours (Young and Kay, supra, 2001; Dunlap, supra, 1999). Two positive activators, Clock and Mop3/Bmal1, regulate expression by interacting with enhancer elements, termed E-boxes. Target genes of these activators include several repressors, including the Per proteins, Per1, Per2, and Per3, and the Cryptochrome molecules, Cry1 and Cry2, which function to inhibit the Clock/Mop3 complex generating a circadian oscillation of 24 hours (see Young and Kay, supra, 2001).

Despite this growing understanding of the mechanism of circadian gene regulation, the link between transcriptional output and physiology under circadian control has been lacking. To address this problem, high density oligonucleotide DNA arrays were used to identify mRNA transcripts exhibiting circadian expression patterns in the SCN and liver of mice entrained to a 12 hr: 12 hr light:dark cycle and subsequently placed in constant darkness (see, also, Panda et al., supra, 2002b). The dataset obtained confirmed the expression of many genes previously known to be circadian regulated, and identified additional circadian regulated genes of known and unknown function in clock control. Analysis of orchestrated expression patterns of these genes revealed transcriptional networks that underlie temporal coordination of physiological processes. A publicly accessible database has been constructed on the world wide web, at the URL "expression.gnf.org\circadian", where users can query for circadian regulated genes in the SCN or liver, or for the temporal expression patterns for their genes of interest.

For these experiments, 7 to 8-week old male C57BL/6J mice were entrained on a 12 hr: 12 hr light: dark cycle for two weeks, then placed in constant darkness for one full day. Ten animals were sacrificed per time point starting at CT18 for two full days every 4 hr. Brains and livers were rapidly dissected under dim red light (15 W Kodak safe lamp filter 1A); the SCN were quickly dissected under bright light in a dissecting microscope and placed in a 5 µl drop of TRIZOL reagent (Invitrogen). Total RNA was prepared, and samples were labeled and hybridized in duplicate (or more) to mouse (U74A) high-density oligonucleotide arrays (GeneChip® Murine Genome U74 Set Version 2; Affymetrix) as previously described (Lockhart et al., *Nat. Biotechnol.* 14:1675, 1996; Wodicka et al., *Nat. Biotechnol.* 15:1359, 1997; Sandberg et al., *Proc. Natl. Acad. Sci. USA* 97:11038, 2000, each of which is incorporated herein by reference). Primary image analysis of the arrays was performed using GENECHIP 3.2 software (Affymetrix), and images were scaled to an average hybridization intensity (average difference) of 200. The COS-OPT algorithm, which generates a p-value (pMMC-beta) and assigns phase, was used to detect cycling genes (see Example 1). Transcripts having a p-value of 0.1 or less were considered cycling, and binned into circadian times every four hours, from CT2 to CT22. Expression patterns for these transcripts were visualized using GENESPRING software (Silicon Genetics; Redwood City Calif.).

The availability of a comprehensive circadian dataset from two different tissues offered an opportunity for a systematic analysis of transcriptional output of the clock. Approximately the same number (approx. 10%) of detectably expressed genes were under circadian control in both SCN and liver. In addition, several genes previously identified as clock regulated such as Cry1, Per2, and Mop3 were detected in the dataset, while others such as Per1 apparently were cycling, but fell below the conservative detection threshold set for the present study.

The peak expression of the identified genes were distributed throughout the circadian cycle, with the most populous clusters in the SCN being CT10 (10 hours after subjective dawn) and CT22, roughly anticipating dusk and dawn, respectively (see Panda et al., supra, 2002b; FIGS. 1A to 1C). 337 SCN and 335 liver transcripts were binned by COSOPT into 6 circadian times (CT). In liver, the largest clusters of circadian regulated transcripts occurred at CT6 and CT14 (see Panda et al., supra, 2002b; FIGS. 1A to 1C), likely reflecting the distinct temporal organization of the different physiologies mediated by the liver (e.g., metabolism). A comparison of overlap between cycling genes in the SCN and liver revealed only 28 genes in common (see Panda et al., supra, 2002b; FIG. 1D), including the clock component, Per2, and several genes whose transcripts were previously not known to (and circadian regulated in) the liver (see Panda et al., supra, 2002b; FIG. 1I and Suppl. FIG. S2; see, also, Lorent et al., *Differentiation* 55:213, 1994). This simple mechanism, however, fails to explain the fact that many genes with detectable and equivalent levels of expression in both tissues cycle only in one of the two tissues. For example, carbon catabolite repression 4 homolog (Ccr4) is expressed at approximately the same levels in the dataset in both SCN and liver, yet only cycles in the liver (see Panda et al., supra, 2002b; FIG. 1I and Suppl. FIG. S2). The previously described circadian pattern of expression of Ccr4 in several other peripheral tissues, including kidney, heart, spleen, and retina, highlights the tissue specific component to circadian transcriptional rhythmicity in mammals (Wang, et al., *BMC Dev. Biol.* 1:9, 2001). These results indicate that a significant percentage of the genome (approximately 10%) is under tissue specific circadian regulation, and underscore the importance of temporal organization for many physiological processes.

TABLE 5

| Probeset | Symbol | Description | Refseq | Unigene | SCN Cosopt.pMMC-Beta | Liver Cosopt.pMMC-Beta |
|---|---|---|---|---|---|---|
| 92809_r_at | Fkbp4 | FK506 binding protein 4 (59 kDa) | NM_010219 | Mm.12758 | 0.072658 | 0.071484 |
| 94018_at | Ub13 | ubiquitin-like 3 | NM_011908 | Mm.21846 | 0.038727 | 0.15764 |
| 95465_s_at | Cacng6 | calcium channel, voltage-dependent, gamma subunit 6 | NM_019432 | Mm.24750 | 0.13146 | 0.046114 |
| 96608_at | Phyh | phytanoyl-CoA hydroxylase | NM_010726 | Mm.27066 | 0.13981 | 0.095547 |
| 94478_at | Rab5a | RAB5A, member RAS oncogene family | NM_025887 | Mm.28872 | 0.17137 | 0.046806 |
| 94485_at | Peci | peroxisomal delta3, delta2-enoyl-Coenzyme A isomerase | NM_011868 | Mm.26863 | 0.17067 | 0.027661 |
| 94489_at | Ptp4a1 | protein tyrosine phosphatase 4a1 | NM_011200 | Mm.28909 | 0.064335 | 0.03399 |
| 99650_at | Csnk1a1 | casein kinase 1, alpha 1 | none | Mm.43737 | 0.19561 | 0.078053 |
| 101585_at | Pgrmc1 | progesterone receptor membrane component 1 | NM_016783 | Mm.9052 | 0.060712 | 0.17849 |
| 102322_at | Ugdh | UDP-glucose dehydrogenase | NM_009466 | Mm.10709 | 0.18791 | 0.10697 |
| 104598_at | Ptpn16 | protein tyrosine phosphatase, non-receptor type 16 | NM_013642 | Mm.2404 | 0.023338 | 0.17969 |
| 94378_at | Rgs16 | regulator of G-protein signaling 16 | none | Mm.181709 | 0.0272 | 0.12929 |
| 97402_at | Temt | thioether S-methyltransferase | NM_009349 | Mm.299 | 0.19641 | 0.10905 |
| 99064_at | Usp4 | ubiquitin specific protease 4 (proto-oncogene) | NM_011678 | Mm.3974 | 0.19906 | 0.08681 |
| 99076_at | Thra | thyroid hormone receptor alpha | none | Mm.26587 | 0.060024 | 0.024133 |
| 99959_at | Ak4 | adenylate kinase 4 | NM_009647 | Mm.42040 | 0.09807 | 0.015789 |
| 100959_at | S100a13 | S100 calcium-binding protein A13 | NM_009113 | Mm.6523 | 0.18727 | 0.11391 |
| 102302_at | Bckdhb | branched chain ketoacid dehydrogenase E1, beta polypeptide | none | Mm.12819 | 0.14236 | 0.16934 |
| 103983_at | Adh4 | alcohol dehydrogenase 4 (class II), pi polypeptide | NM_011996 | Mm.25845 | 0.19113 | 0.032683 |
| 92532_at | Avpr1a | arginine vasopressin receptor 1A | NM_016847 | Mm.4351 | 0.019388 | 0.071942 | cycle (see, also, Table 5). Genes that cycle in all output tissues can represent basic cellular outputs or critical components of the circadian clock (e.g., Per2). Most genes, including Per2, were delayed in peak expression in liver as compared to the SCN, usually by about 4 hr to 8 hr. However, several genes, including tubulin-5 (Tubb5) and a transforming growth factor-1-induced transcript (Tgfb1i4), were coordinately regulated with the same phase in both tissues.

To further investigate the overlap in cycling genes between the SCN and liver, the average level of expression was determined for each cycling gene in both tissues. The distribution of liver cycling transcripts in SCN and liver by abundance was determined, and the relative abundance of each transcript (average AD value across time course) was obtained for liver cycling transcripts (pMMC-beta<0.1) from the liver and SCN. Similar results were obtained when comparing the relative abundance of SCN cycling transcripts in SCN and liver. This analysis revealed that a significant number of cycling genes in the liver do not cycle in the SCN because they are not detectably expressed there. Murinoglobulin 2 (mug2), is an example of such a gene, whose expression is tightly restricted To gain insight into the mechanism of circadian transcriptional regulation at the level of promoter elements, recently available mammalian genome sequences (Lander et al., *Nature* 409:860, 2001; Venter et al., *Science* 291:1304, 2001) were utilized to identify output genes had response elements in their structural genes indicative of the core Clock/Mop3 complex (CACGTGA; Hogenesch et al., *Proc. Natl. Acad. Sci. USA* 95:5474, 1998). Probe sets for all cycling genes were mapped to Unigene using BLAST (Altschul et al., *J. Mol. Biol.* 215:403, 1990) as previously described (Hogenesch et al., *Cell* 106:413, 2001, which is incorporated herein by reference). The first 300 coding nucleotides of each complete Unigene cluster that harbored a translational methionine were used as bait sequences to search the Celera Mouse Assembly (r12 masked) using BLAST. Hits were indexed up to 10 kb upstream of the translational methionine (when available), and used to find the consensus Clock/Mop3 consensus site, CACGTGA.

This analysis revealed a circadian distribution of this element in the SCN with a peak at CT10 to CT14. The distribution of occurrences of Clock/Mop3 binding site in upstream regions of SCN cycling genes was determined, and the number of occurrences of the Clock/Mop3 consensus site was counted upstream of the translational methionine, at 2 kb, 3 kb, 5 kb, and 10 kb in the structural genes representing transcripts for each circadian phase. A specificity score was generated that takes into account the length of the promoter sequences retrieved for each transcript and the number of cycling transcripts from each cluster. The SCN cluster harbored a previously identified E-box element in the Per1 promoter, as well as several structural genes whose expression was unknown to be regulated in a circadian fashion or by the Clock/Mop3 complex (see Table 6; SEQ ID NOS:1-14; Gekakis, et al., *Science* 280:1564, 1998). These transcripts included a regulator of G-protein signaling-16 (Rgs16), presenilin 2 (Psen2), and protein tyrosine phosphatase, non-receptor type 16 (Ptpn16). The presence of this element in more than one cluster (e.g., CT22) indicates that other cis-acting elements, trans-activating factors, or post-transcriptional mechanisms such as mRNA stability also are involved in generating coordinated circadian output.

TABLE 6

| | |
|---|---|
| AGCCACGTGAGG | Per1 |
| AGCCACGTGACA | Per1 |
| CTTCACGTGAGG | Per2 |
| CCCCACGTGAAC | 1500039N14Rik |
| AGTCACGTGAGC | FLJ20093 |
| AAGCACGTGATG | Atp6a2 |
| AAGCACGTGACT | Atp6a2 |
| TAGCACGTGACC | Cckar |
| TAACACGTGAGC | Ms4a2 |
| CTCCACGTGACA | Psen2 |
| TGTCACGTGACT | Rgs16 |
| GAACACGTGACT | Ub13 |
| AGACACGTGACC | Ptpn16 |
| GRACACGTGACC | M34 element |

The expression pattern of SCN cycling genes harboring a Clock/Mop3 consensus site was determined, and expression patterns for genes harboring a Clock/Mop3 response element within 3 kb of the translational methionine from the CT10 and CT14 phases were identified. Table 6 shows the sequence and identity of cycling genes harboring Clock/Mop3 site (SEQ ID NOS:1-14). The core CACGTGA Clock/MOP3 consensus site from each gene in the above cluster is indicated along with flanking nucleotides. Also included is the sequence of two previously described sites from the Per1 promoter and a closely related site from the Per2 promoter. When two sites were found in a single promoter region, both are indicated. Gene names are derived from Refseq (Pruitt et al., *Trends Genet.* 16:44, 2000).

Protein Biosynthesis in the SCN

To investigate the physiology under circadian control in the SCN, the cycling genes were organized by circadian phase. This analysis revealed that the largest group of coordinately cycling transcripts share a common function in protein synthesis. More than 20 transcripts representing cytoplasmic ribosomal protein components and 13 transcripts representing mitochondrial ribosomal proteins showed coordinate cycling with a peak phase of expression at CT22 (see Panda et al., supra, 2002b; see FIG. 3A, showing that ribosomal protein transcripts and Sui1, and FIG. 5C, showing that protein processing components (NAC, Srp14, Srp9, Sec61γ) peak during night in the SCN, but not in liver (compare FIGS. 3B and 3D, respectively). The first and rate-limiting step in ribosome biogenesis in nucleoli is the synthesis of ribosomal RNAs mediated by the multisubunit RNA polymerase I and its accessory factors (Larson et al., *Biochem. Cell Biol.* 69:5, 1991). While none of the core RNA Pol I subunits exhibited any significant transcriptional rhythm, a component shared by all three RNA polymerases—metallothionein 1 activator—exhibited a rhythm in peak phase with the ribosomal protein transcripts. Transcriptional control of a common subunit of all three polymerases can ensure coordinated regulation of both rRNA and ribosomal protein transcription. Additionally, transcript levels of TAF Ib, which is a component of the SL1 complex that recruits RNA Pol I to rRNA promoters, and topoisomerase I, which is essential for RNA pol I mediated transcription, cycle in similar phases.

The control points in ribosome biogenesis and the half-lives of ribosomes exhibit great variability with tissue types. As such, SCN neurons may have adapted a temporal component of ribosome turnover to possibly enhance protein synthesis. In support of this role, diurnal changes in morphology and size of nucleoli in the rat supraoptic nucleus and superior cervical neurons have been observed (Seite and Pebusque, *Chronobiol. Internatl.* 2:69, 1985; Bessone and Seite, *Cell Tiss. Res.* 240:393, 1985). Proper initiation complex formation and fidelity of translational initiation is another mechanism adapted by organisms to enhance protein synthesis, particularly during stress. One key regulator of this mechanism is Sui-1 (Cui et al., *Mol. Cell. Biol.* 18:1506, 1998), which was first identified in yeast. Transcription of Sui-1 is clock regulated in *Arabidopsis* (see Harmer et al., supra, 2000) and, as disclosed herein, in *Drosophila* (Example 1) and in mouse, including in both liver and SCN. In the SCN, however, the peak phase of Sui-1 expression is delayed 8 hr from the peak phase of ribosomal proteins. As such, cycling of both ribosome biogenesis and of Sui-1 can be involved in enhancing translation at different times of day. Importantly, trough levels of several of these key components remained relatively high, indicating that a basal level of protein synthesis is sustained throughout the circadian cycle. Finally, none of these ribosomal components exhibited any significant circadian transcriptional control in liver, indicating that temporal regulation of protein synthesis in the liver offers no advantage (see Panda et al. supra, 2002b, FIG. 3B). The results of in situ hybridization, which was performed as previously described by Bunger et al. (*Cell* 103:1009, 2000, which is incorporated herein by reference) revealed a signal from the SCN region at peak and trough levels of expression supports cycling of the ribosomal protein gene Rpl41 (see Panda et al., supra, 2002b; FIG. 3F).

Several genes involved in steps subsequent to translation are also clock regulated, including gene products that participate in protein folding, targeting to endoplasmic reticulum (ER), post-translation modification, and vesicle transport. Shortly after initiation of translation, two different cytoplasmic complexes, dimeric nascent polypeptide-associated complex (NAC), and multimeric ribonucleoprotein complex signal recognition particle (SRP), compete for binding to the nascent polypeptide exiting the ribosome (Raden and Gilmore, *Mol. Biol. Cell* 9:117, 1998). SRP selects signal-containing ribosomes for targeting, while binding of NAC prevents targeting of signal peptide-less nascent chains to the ER membrane. Once SRP binds to and docks proper ribosomes to the ER, the subsequent step of protein translocation requires the trimeric Sec61p complex. Oligomers of the Sec61 complex form a transmembrane channel where proteins are translocated across and integrated into the ER membrane (Jungnickel and Rapoport, *Cell* 82:261, 1995). The Sec61 complex has also been implicated in translocation of misfolded proteins from the ER to the cytosolic protein degrading machinery, thereby ensuring folding of newly synthesized proteins with fidelity (Romisch, *J. Cell. Sci.* 112:

4185, 1999). As disclosed herein, constituents of NAC, SRP (SRP9, SRP14) and Sec61γ exhibited coordinated cycling in phase with the ribosomal cluster. In this manner, protein synthesis and processing are circadian regulated in the SCN to ensure that this process is coordinately regulated throughout the night.

Redox and Energy Flux in the SCN

The observation that several genes involved in energy production exhibit circadian rhythms in their steady state mRNA levels indicates that this process is under clock control. These include components involved in carbon utilization, oxidative phosphorylation, and interconversion of nucleotide triphosphates. The transcripts of three major enzymes, hexokinase1 (Hk1), malate dehydrogenase, and mitochondrial 3-ketoacyl-CoA thiolase cycled in the SCN. This results is consistent with previous observations that 2-deoxyglucose utilization exhibits a marked circadian oscillation (Schwartz and Gainer, *Science* 197:1089, 1977). While Hk1 and malate dehydrogenase mediate the use of glucose as an energy source, mitochondrial 3-ketoacyl-CoA thiolase regulates the use of ketone bodies as the major energy source in neurons. Reducing power derived from the breakdown of glucose and ketone bodies is ultimately used in mitochondrial oxidative phosphorylation to generate ATP. An example of a gene involved in interconversion of NTPs is nucleotide diphosphate kinase 3, ndk3, which, as disclosed herein, is circadian regulated and peaks at CT22. In addition to these genes, more than 20 components of mitochondrial energy production were coordinately regulated and clustered at CT22 (see Panda et al., supra, 2002b; FIGS. 5A and 5B). FIG. 5A illustrates the mitochondrial oxidative phosphorylation pathway, i.e., transfer of electron from NADH to molecular oxygen, with concomitant ATP production, which occurs in the mitochondrial membrane in four multi-subunit complexes. Components of these complexes are encoded by both the mitochondrial and nuclear genomes. FIG. 5B shows that at least seven nuclear components of complex I, one each of complex II and complex III, and six of complex IV peak during night. The resulting proton motif force is used by multi-subunit F-type ATPases to generate ATP from ADP. Three components of the F-type ATPase, and mitochondrial ADP/ATP translocase 2 peak during night. Data traces are in blue, genes involved in carbon substrate metabolism are in orange. An in situ hybridization signal of 2900010C23Rik was observed. A putative NADH dehydrogenase (ubiquinone) flavoprotein 2 (Ndufv2) supports its cycling. These results indicate that expression of these genes anticipate impending diurnal neuronal activity.

Cell Signaling

An important circadian output cluster in the SCN includes genes involved in neurosecretory processes and signaling. Coordinated expression of transcripts from genes involved in prohormone processing, vesicle transport and fusion, and late endosomal processing, occurred during the anticipation of dawn and dusk (see Panda et al., supra, 2002b; FIGS. 4A to 4C). In situ hybridization signals obtained for Sgne1 (GenBank Acc. No. NM_009162), secretogranin III (Sg3; NM_009130), and Kcnma1 (NM_010610) supported their cycling. A secretory granule protein, Sgne1, previously shown to activate prohormone convertase 2 (PC-2; Braks and Martens, *Cell* 78:263, 1994), exhibited a circadian rhythm in its transcript expression. PC-2 has been implicated in the processing of several neuropeptides including somatostatin (Mackin et al., *Endocrinology* 129:2263, 1991), an inhibitory neurotransmitter that also is circadian regulated to the same phase as Sgne1. As such, Sgne1 can be involved in accentuating the circadian expression of somatostatin, resulting in a protein rhythm with a peak at CT4 (see Shinohara et al., *Neurosci. Lett.* 129:59, 1991). Another secretory granule protein, secretogranin III (Scg3), also exhibited clock regulation.

Several components involved in vesicle trafficking were identified as circadian regulated to two distinct phases. AP4-sigma, which is involved in trans-Golgi cycling (Hirst et al., *Mol. Biol. Cell* 10:2787, 1999), synapsin 1, which is implicated in maintenance of a release ready pool of presynaptic vesicles (Li et al., *Proc. Natl. Acad. Sci. USA* 92:9235, 1995), and Vps29, which is involved in recycling components from the endosome to the trans-Golgi (Seaman et al., *J. Cell Biol.* 137:7992, 1997), all cycled with the same phase as Sgne1 and somatostatin. In contrast, Snap25 and Munc18c (Jahn, *Neuron* 27:201, 2000), which mediate vesicle fusion, Eps15, which is implicated in vesicle recycling (Salcini et al., *Nat. Cell Biol.* 3:755, 2001), and Vps4b, which is involved in late endosomal vesicle transport (Yoshimori et al., *Mol. Biol. Cell* 11:747, 2000), all cycled with a peak in the late subjective day, CT10. Finally, the mRNA level of several prohormones and peptide neurotransmitters such as proopiomelanocortin (Pomc), adenylate cyclase activating polypeptide 1 (Pacap), cholecystokinin, somatostatin, and PDGF-a exhibited clock regulation in the SCN.

Additional molecules, such as arginine-vasopressin (AVP), vasopressin receptor-1A, somatostatin, PACAP-1, enkephalin, galanin, calcitonin-gene related peptide (CGRP), were reported to cycle at the mRNA levels in SCN tissue (Ibata et al., *Front. Neuroendocrinol.* 20:241, 1999). In addition to confirming many of these genes in the dataset obtained in this study, rhythms in mRNA levels of genes involved in biosynthesis of non-peptide neurotransmitters such as GABA, histamine, and dopamine also were observed. These results indicate that clock regulation of neurotransmission is more elaborate than previously thought, and also underscore the importance of neurosecretion as an important function of SCN physiology and draw a direct connection to the circadian transcriptional apparatus.

Circadian Gene Regulation in the Liver

As the master regulator of circadian rhythms in mammals, the SCN must coordinate peripheral physiologies under its control. Behavioral control of feeding, for example, must coordinate with metabolic processes to achieve efficiency in nutrient uptake and utilization. This regulation need not be direct, as the SCN can regulate liver circadian function by regulating feeding behavior. The SCN pacemaker communicates with the arcuate nucleus (ACN), which is the hypothalamic appetite control center. Rhythms in various orexigenic (NPY, AGRP, Galanin, etc.), and anorexogenic (leptin, insulin, αMSH, glucagon, etc.) signals and plasma hormonal signals ultimately result in a feeding rhythm that is entrained to activity-arousal mechanisms in the light-dark cycle (Schwartz et al., *Nature* 404:661, 2000). Rodents entrained to a light-dark cycle and subsequently free run in constant darkness exhibit a rhythm in their feeding, where they consume more than 70% of their daily food intake during nighttime activity (Poirel and Larouche, *Chronobiologia* 13:345, 1986). Food intake may in turn entrain the peripheral clock in the liver. Recent evidence supports this hypothesis by showing that the liver clock can be dissociated from the central oscillator in SCN by restriction of feeding (Stokkan et al., *Science* 291:490, 2001).

Energy Metabolism

Circadian rhythms were detected in the transcription of many genes involved in nutrient uptake and utilization. Temporal regulation optimizes use of absorbed nutrients for energy generation and storage during feeding, and a switch to stored and alternative energy sources during fasting. Coordinated circadian regulation of glucose transporters, glucagon receptor, and rate-limiting steps in the metabolism of hexose sugars were observed with a peak phase of expression in early evening (see Panda et al., supra, 2002b; FIG. 6A, which provides an overview of glucose and fatty acid metabolism in liver (cycling enzymes and transporters are shown in blue), and FIG. 6B, which demonstrates that components of gluconeogenesis, glycolysis, and fatty acid metabolism peak during night, when the animals consume the majority of their diet; GLUT1 and GLUT5 are known to cycle in intestine during night (Rhoads et al., *J. Biol. Chem.* 273:9510, 1998; Castello et al., *Biochem. J.* 309:271, 1995); see, also, FIG. 6C, which demonstrates that a putative regulator of fatty acid utilization, lipin (Peterfy et al., *Nat. Genet.* 27:121, 2001), cycles with a peak expression during day; cycling of lipin from microarray dataset (in purple, and 2nd y-axis) was confirmed independent by real time PCR (in black; Bunger et al., supra, 2000)).

This regulation facilitates glycogen synthesis during feeding and use of hexose sugars as a primary energy source for up to few hours in the post-adsorptive period (Arias, et al., "The Liver: Biology and Pathophysiology" 4th ed. (Lippincott Williams & Wilkins, Philadelphia, Pa., 2001). Similarly, the clock facilitates the use of short- and medium-chain fatty acids during nighttime feeding and of stored very long-chain fatty acids during the day.

Cholesterol Metabolism

Transcription of genes involved in cholesterol biosynthesis and metabolism also was under circadian control. In the liver, a significant portion of acetoacetyl CoA is converted to 3-hydroxy-3-methylglutaryl-CoA (HMGCoA), the starting compound in cholesterol biosynthesis. Its metabolism is subject to clock regulation across species, as in plants (Harmer et al., supra, 2000), flies (Example 1), and mice, the transcription of HMGCoA lyase is under clock control. In mammals, the conversion of HMGCoA to mevalonate by HMGCoA reductase (HMGCoAR) is an additional clock-controlled step (Shapiro and Rodwell, *Biochem. Biophys. Res. Comm.* 37:867, 1969). Clock control of this step has long been thought to underlie the circadian rhythm in plasma cholesterol level in mammals. However, four additional enzymes of cholesterol synthesis also exhibited coordinated cycling of their transcript levels (see Panda et al., supra, 2002b; FIG. 7A, which provides an overview of cholesterol synthesis pathway in animals (Michal, "Biochemical Pathways", G. Michal, Ed. (John Wiley & Sons, Inc., New York, 1999)); reactions from 3-carbon acetyl CoA up to 15-carbon (C15) trans-trans farnesyl-PP take place in peroxisome and cytosol; steps after the clock mediated condensation of two C15 units to form squalene proceed on the ER; degradation of cholesterol produces different steroids, and finally bile acid; and FIG. 7B, which demonstrates that enzymes of cholesterol biosynthesis (in blue) peak during the night). Coordinated cycling of several biosynthetic enzymes can ensure a tight clock regulation of cholesterol production. While cholesterol synthesis is phased to the subjective day when dietary cholesterol supply is low, the degradation products of cholesterol (steroids and biles) are produced at different times of the day. Reflective of this, transcripts of many cytochrome P450 gene products and enzymes involved in cholesterol catabolism were found to be clock regulated and phased to different times of the day (see Panda et al., supra, 2002b; FIG. 7A, and FIG. 7C, which demonstrates that enzymes of cholesterol degradation peak at different times of the day; see, also, Kornmann et al., *Nucleic Acids Res.* 29:E51, 2001); see, also, FIG. 7D, demonstrating that transcription of three membrane channel proteins, Mrp2, Slc22a1, and Slc22a2, which transport bile acids and organic cations, cycle; and FIG. 7E, showing a cycling trace of Cyp7a (in blue) and was confirmed by real time PCR (black).

Bile Acid and Xenobiotic Metabolism

Transcripts from genes involved in several aspects of bile acid metabolism also were under circadian control. The liver is the only organ that converts cholesterol to bile acids and uses a set of enzymes with broad substrate specificity for the breakdown and excretion of cholesterol and of many xenobiotics. This process has been described as two phased, with the first phase consisting of side group oxidation and hydroxylation, and the second involving the addition of a polyatomic group such as sulfate, glutathione, glucuronate, or an amino acid such as glycine or taurine. These processes change the bioactive properties of many substrates and enhance their solubility at acidic pH. More than 10 cytochrome P450 genes and related genes mediating the phase I oxidation of cholesterol were found to be clock regulated. Synthesis of conjugation partners such as taurine and glycine or enzymes of the second phase biotransformation, such as GST also were under clock control. Cysteine dioxygenase (Cdo) catalyzes reduction of cysteine to 3-sulfinoalanine, whose subsequent metabolism produces taurine and sulfite (Michal, supra, 1999).

Enzymes mediating the activation of sulfite also were clock regulated, as the enzyme 3'-phosphoadenosine 5'-phosphosulfate synthase 2 (Papss2), which mediates this conversion of sulfite to high energy PAPS, exhibited clock regulated transcription. Methylation of many xenobiotics also alters their activity, and, in this respect, four methyltransferases, including betaine-homocysteine methyl transferase (Bhmt), nicotinamide N-methyltransferase (Nnmt), thioether S-methyltransferase (Temt), and thiopurine methyltransferase (Tpmt) exhibited circadian regulation.

The activities of most methyltransferases are fine-tuned by cellular concentrations of S-adenosylhomocysteine (SAH). Clock regulated transcript levels of SAH hydrolase, which catalyzes the reversible hydrolysis of SAH to adenosine (Ado) and L-homocysteine (Hcy), also was clock regulated. This reaction regulates the intracellular SAH concentration.

Conjugated bile acids and biotransformed xenobiotics are excreted from hepatocytes by different membrane transporters, some of which are regulated by the circadian clock. The organic cation transporters Slc22a1 and Slc22a2, which transport choline and polyamines, also exhibited clock regulation at transcript level. Substrates for Mrp2 include bile acid conjugates, glutathione-, glucuronate-, and anionic conjugates of both endobiotics and xenobiotics (Kullak-Ublick et al., *J. Hepatol.* 32:3, 2000). Clock regulated transcription of components of xenobiotic metabolism and excretion can account for observed chronotoxicity of a large number of drugs and drug metabolites (Focan, *Pharmacol. Ther.* 67:1, 1995).

Intermediate Metabolism

In addition to the well described clock regulation of steroid metabolism, by the clock, (Layery et al., *Mol. Cell Biol.* 19:6488, 1999; Wuarin et al., *J. Cell Sci.* Suppl 16:123, 1992), the present study revealed cycling transcript levels of many enzymes involved in intermediate metabolism. The liver is the major site of synthesis of many bioactive molecules such as nuclear receptor ligands (e.g., tri-iodo-thyronine, "T3"), retinoid, polyamines, cofactors, and the oxygen carrier heme. Retinoic acid and T3 can bind directly to nuclear receptors and affect transcription. The thyroid gland releases inactive thyroxine (T4) into blood circulation, which is deionized to active T3 by the liver enzyme deiodinase-1 (Dio1). Clock regulated synthesis and release of T4 from the thyroid has long been considered as the underlying mechanism in maintaining a daily rhythm in serum T3. This proposed mechanism, however, fails to explain a daily rhythm of plasma T3 in hypothyroidism patients receiving exogenous T4. The clock-regulated hepatic transcript levels of Dio1 identified in the dataset obtained in the present study better explains the above described clinical observation.

Transcript levels of two enzymes, retinol dehydrogenase 7 (Rdh7), and retinal short-chain dehydrogenase/reductase-1 (Rsdr1-pending), also cycled. Clock regulation of these two enzymes, which act upon all-trans retinal produced in a one step reaction from dietary β-carotene (from plants), indicates that synthesis of the nuclear receptor ligand, retinoic acid, and of the visual photopigment, retinol, from all-trans-retinal also is under clock control. In plants, a putative β-carotene hydroxylase that converts β-carotene to zeaxanthine and related photoprotective pigments xanthophylls is under clock control (Harmer et al., supra, 2000; Michal, supra, 1999). As such, the circadian metabolism of β-carotene is conserved across organism as diverse as plants and animals, demonstrating evolutionary pressure in regulated synthesis of major light sensing pigments in such organisms.

In addition to light reactions, β-carotene metabolites are also major scavengers of reactive oxygen species, and help maintain a physiologically viable redox state. Heme, however, is the most extensively used biological sensor of cellular redox state. The first committed and physiologically irreversible step in heme biosynthesis is the condensation of glycine and succinyl coenzyme A to yield delta-aminolevulinic acid (ALA). Clock control of ALA-synthase 1 (Alas1) transcription in flies and mammals, and of many additional enzymes in the subsequent reactions in plants, demonstrates that clock-regulated production of the cellular redox sensors is conserved through evolution.

In summary, a global analysis of circadian patterns of transcription from the core pacemaker in the SCN and from an important physiological mediator, the liver, revealed that as much as 10% of the mammalian transcriptome is under circadian control, that many of these clock controlled genes constitute rate-limiting steps in important physiological processes, and that the expression of particular subsets of circadian controlled genes are tissue specific. These results highlight the fundamental importance of circadian rhythms to an organism as a whole, and demonstrate that the circadian system has evolved to encompass different signaling pathways and mechanisms to generate tissue specific transcriptional rhythms. In addition, evolution has devised an effective circadian control of physiology by targeting key components of pathways. Thus, just as biochemical pathways have been conserved over millions of years, circadian control of such pathways also has been conserved.

The analysis of clock regulated transcription in the fly (Example 1) indicates that several clock regulated pathways, including heme biosynthesis (Alas1), cholesterol metabolism (HMGCoA lyase), neuropeptide signaling (Dbi), neuronal excitability (kcnma1/slowpoke), energy metabolism (hexokinase), and metabolism (glutathione S-transferase and cytochrome P450's) has been conserved over more than 600 million years of evolution. Thus, cross-species conservation of clock regulated transcription can suggest a key role of a component in a given process. For example, the human homologue of a neuronal nicotinic receptor b2 (Chrnb2), which cycles in mouse SCN, is mutant in nocturnal frontal lobe epilepsy, suggesting that Chrnb2 is involved in rhythmic control of motor coordination (De Fusco et al., Nat. Genet. 26:275, 2000; Phillips et al., Am. J. Hum. Genet. 68:225, 2001). Similarly, the results in Example 1 indicate that a large conductance calcium activated potassium channel (Kcnma1) has a key role in activity rhythms. Conserved clock regulated expression of Kcnma1 in the SCN, and the recent finding of an important role of potassium ions in SCN function indicates that Kcnma1 represents a conserved mechanism for clock coordination and regulation of activity across species.

EXAMPLE 3

Screening Assays for Sleep/Wake Cycle Modulating Agents

This example provides methods for screening BK channels, including methods adaptable to high throughput formats.

A small molecule screen for a perturbagen (i.e., an agonist or an antagonists) of a BK channel can utilize a cell line genetically modified to express a BK channel by stable transfection or by transient transfection. Channel activity can be measured, for example, by investigating accumulation of a fluorescent indicator dye in the cells due to passage through BK channels. These signals can be measured using fluorescent plate readers such as fluorescence macro-confocal high throughput screening (FMAT; Applied Biosystems) using a robotic system that allows for the assaying of thousands or more of independent perturbagens in an arrayed or other format. By adding one or a combination of small molecules or other perturbagens to wells and screening them in such format, agonists or antagonists of BK channels can be identified.

Although the invention has been described with reference to the above examples, it will be understood that modifications and variations are encompassed within the spirit and scope of the invention. Accordingly, the invention is limited only by the following claims.

What is claimed is:

1. A method of identifying an agent that can modulate the sleep/wake cycle in a subject, the method comprising:

contacting a test system comprising a BK channel and a cognate BK channel binding protein with an agent suspected of having the ability to modulate the sleep/wake cycle in the subject, wherein the BK channel comprises a *Drosophila* slowpoke (slo) polypeptide, or an ortholog thereof, wherein the ortholog is human slo, murine slo, rat slo, or rabbit slo;

detecting a change in:

i) conformation of the BK channel or protein-protein interaction between the BK channel and the BK channel binding protein, and ii) intracellular ions induced by the agent as compared to the same measurements taken in the absence of the agent, thereby identifying an agent that modulates BK channel activity;

administering the agent that modulates BK channel activity to a test subject; and thereafter detecting a change in the sleep/wake cycle of the test subject, thereby identifying an agent that can modulate the sleep/wake cycle in a subject.

2. The method of claim 1, wherein the ortholog is a human ortholog of the slo polypeptide.

3. The method of claim 1, wherein the ortholog is a mouse slo polypeptide.

4. The method of claim 1, wherein the BK channel comprises a mutant BK channel.

5. The method of claim 1, wherein the test system comprises a substantially purified BK channel polypeptide, and wherein said contacting is performed in vitro.

6. The method of claim 1, wherein the test system comprises a membrane containing the BK channel, and wherein said contacting is performed in vitro.

7. The method of claim 6, wherein the membrane containing the BK channel comprises an isolated cell membrane.

8. The method of claim 7, wherein the cell membrane is a muscle cell membrane or a nerve cell membrane.

9. The method of claim 6, wherein the membrane containing the BK channel comprises a liposome.

10. The method of claim 1, wherein the test system comprises a cell delimited by a cell membrane, or a cell membrane isolated from said cell, and wherein the BK channel is expressed in the cell membrane.

11. The method of claim 10, wherein the BK channel is endogenous to the cell.

12. The method of claim 10, wherein the BK channel is expressed from a heterologous nucleic acid molecule.

13. The method of claim 12, wherein the BK channel is a *Drosophila* slo polypeptide.

14. The method of claim 12, wherein the BK channel is a mutant *Drosophila* slo polypeptide or a mutant of a human ortholog of *Drosophila* slo polypeptide.

15. The method of claim 12, wherein the cell further expresses an endogenous BK channel binding protein.

16. The method of claim 15, wherein the BK channel binding protein is a *Drosophila* slob polypeptide or an ortholog thereof.

17. The method of claim 15, wherein the BK channel binding protein is a β subunit of a BK channel.

18. The method of claim 10, wherein the cell is a muscle cell or a nerve cell.

19. The method of claim 10, wherein the cell is a *Xenopus* oocyte.

20. The method of claim 10, wherein the cell is substantially isolated, and wherein said contacting is performed ex vivo.

21. The method of claim 10, wherein the cell is in an organism, and wherein said contacting is performed in vivo.

22. The method of claim 21, wherein the organism is a transgenic non-human organism.

23. The method of claim 22, wherein the transgenic non-human organism comprises a transgene encoding the BK channel.

24. The method of claim 1, wherein the agent is a polynucleotide, a peptide, a peptidomimetic, a peptoid, or a small organic molecule.

25. The method of claim 1, wherein the agent increases the activity of the BK channel.

26. The method of claim 1, wherein the agent decreases the activity of the BK channel.

27. The method of claim 1, wherein the activity of the BK channel is detected using an electrophysiological method.

28. The method of claim 27, wherein the electrophysiological method is a patch-clamp assay or a voltage clamp recording.

29. The method of claim 1, wherein the activity of the BK channel is detected using a fluorescent dye assay or a rubidium ion flux assay.

30. The method of claim 29, wherein the fluorescent dye is fura-2 or indo-1.

31. The method of claim 1, wherein the activity of the BK channel is detected by detecting a conformational change in the BK channel.

32. The method of claim 1, further comprising detecting a conformational change in the BK channel using a fluorescence resonance energy transfer assay.

33. The method of claim 1, wherein the activity of the BK channel is detected using Fourier transform infrared resonance spectroscopy, Raman spectroscopy, fluorescence polarization, or atomic force microscopy.

* * * * *

SEQUENCE LISTING

<160> NUMBER OF SEQ ID NOS: 14

<210> SEQ ID NO 1
<211> LENGTH: 12
<212> TYPE: DNA
<213> ORGANISM: Mouse

<400> SEQUENCE: 1
agccacgtga gg

```
<210> SEQ ID NO 2
<211> LENGTH: 12
<212> TYPE: DNA
<213> ORGANISM: Mouse

<400> SEQUENCE: 2
agccacgtga ca                                                              12

<210> SEQ ID NO 3
<211> LENGTH: 12
<212> TYPE: DNA
<213> ORGANISM: Mouse

<400> SEQUENCE: 3
cttcacgtga gg                                                              12

<210> SEQ ID NO 4
<211> LENGTH: 12
<212> TYPE: DNA
<213> ORGANISM: Mouse

<400> SEQUENCE: 4
ccccacgtga ac                                                              12

<210> SEQ ID NO 5
<211> LENGTH: 12
<212> TYPE: DNA
<213> ORGANISM: Mouse

<400> SEQUENCE: 5
agtcacgtga gc                                                              12

<210> SEQ ID NO 6
<211> LENGTH: 12
<212> TYPE: DNA
<213> ORGANISM: Mouse

<400> SEQUENCE: 6
aagcacgtga tg                                                              12

<210> SEQ ID NO 7
<211> LENGTH: 12
<212> TYPE: DNA
<213> ORGANISM: Mouse

<400> SEQUENCE: 7
aagcacgtga ct                                                              12

<210> SEQ ID NO 8
<211> LENGTH: 12
<212> TYPE: DNA
<213> ORGANISM: Mouse

<400> SEQUENCE: 8
tagcacgtga cc                                                              12

<210> SEQ ID NO 9
<211> LENGTH: 12
<212> TYPE: DNA
<213> ORGANISM: Mouse

<400> SEQUENCE: 9
taacacgtga gc                                                              12
```

```
<210> SEQ ID NO 10
<211> LENGTH: 12
<212> TYPE: DNA
<213> ORGANISM: Mouse

<400> SEQUENCE: 10
ctccacgtga ca                                                         12

<210> SEQ ID NO 11
<211> LENGTH: 12
<212> TYPE: DNA
<213> ORGANISM: Mouse

<400> SEQUENCE: 11
tgtcacgtga ct                                                         12

<210> SEQ ID NO 12
<211> LENGTH: 12
<212> TYPE: DNA
<213> ORGANISM: Mouse

<400> SEQUENCE: 12
gaacacgtga ct                                                         12

<210> SEQ ID NO 13
<211> LENGTH: 12
<212> TYPE: DNA
<213> ORGANISM: Mouse

<400> SEQUENCE: 13
agacacgtga cc                                                         12

<210> SEQ ID NO 14
<211> LENGTH: 12
<212> TYPE: DNA
<213> ORGANISM: Mouse

<400> SEQUENCE: 14
gracacgtga cc                                                         12
```